US009215996B2

(12) United States Patent
Lee et al.

(10) Patent No.: US 9,215,996 B2
(45) Date of Patent: Dec. 22, 2015

(54) APPARATUS AND METHOD FOR OBJECTIVELY DETERMINING HUMAN RESPONSE TO MEDIA

(75) Inventors: Hans C. Lee, Carmel, CA (US); Josh Wilson, Spokane, WA (US); Michael Fettiplace, Madison, WI (US); Michael J. Lee, Carmel, CA (US)

(73) Assignee: THE NIELSEN COMPANY (US), LLC, New York, NY (US)

( * ) Notice: Subject to any disclaimer, the term of this patent is extended or adjusted under 35 U.S.C. 154(b) by 1329 days.

(21) Appl. No.: 11/681,265

(22) Filed: Mar. 2, 2007

(65) Prior Publication Data

US 2008/0214902 A1    Sep. 4, 2008

(51) Int. Cl.
*A61B 5/00*     (2006.01)
*A61B 5/16*     (2006.01)
*A61B 5/0476*   (2006.01)
*A61B 5/1455*   (2006.01)

(52) U.S. Cl.
CPC . *A61B 5/16* (2013.01); *A61B 5/165* (2013.01); *A61B 5/6814* (2013.01); *A61B 5/0476* (2013.01); *A61B 5/1455* (2013.01); *A61B 5/7257* (2013.01); *A61B 2562/0219* (2013.01)

(58) Field of Classification Search
CPC .. A61B 5/04001–5/04004; A61B 2018/00839; A61B 5/165; A61B 2562/0219; A61B 5/0476; A61B 5/1455; A61B 5/7257; A61B 5/6814; A61B 5/16; G06F 2203/00; G06F 3/00; G06F 2203/011–2203/015
USPC .......................................... 600/378, 544–545
See application file for complete search history.

(56) References Cited

U.S. PATENT DOCUMENTS

| | | | |
|---|---|---|---|
| 4,695,879 | A | 9/1987 | Weinblatt |
| 4,755,045 | A | 7/1988 | Borah et al. |
| 4,846,190 | A | 7/1989 | John |
| 4,931,934 | A | 6/1990 | Snyder |
| 4,974,602 | A | 12/1990 | Abraham-Fuchs et al. |
| 5,024,235 | A | 6/1991 | Ayers |
| 5,243,517 | A | 9/1993 | Schmidt et al. |
| 5,406,957 | A | 4/1995 | Tansey |
| 5,447,166 | A | 9/1995 | Gevins |
| 5,450,855 | A | 9/1995 | Rosenfeld |
| 5,513,649 | A * | 5/1996 | Gevins et al. ................. 600/544 |

(Continued)

FOREIGN PATENT DOCUMENTS

| | | |
|---|---|---|
| EP | 1052582 | 11/2000 |
| EP | 1389012 | 2/2004 |

(Continued)

OTHER PUBLICATIONS

Form PCT/ISA/220, PCT/US07/15019, "PCT Notification of Transmittal of The International Search Report and the Written Opinion of the International Searching Authority, or the Declaration," 1 pg.

(Continued)

*Primary Examiner* — William Thomson
*Assistant Examiner* — Shirley Jian
(74) *Attorney, Agent, or Firm* — Hanley, Flight & Zimmerman LLC

(57) ABSTRACT

An exemplary embodiment providing one or more improvements includes a media analysis apparatus and method in which human mental response to media is objectively determined.

64 Claims, 13 Drawing Sheets

(56) References Cited

U.S. PATENT DOCUMENTS

| | | | |
|---|---|---|---|
| 5,579,774 A | 12/1996 | Miller et al. | |
| 5,601,090 A | 2/1997 | Musha | |
| 5,649,061 A | 7/1997 | Smyth | |
| 5,676,138 A | 10/1997 | Zawilinski | |
| 5,692,906 A | 12/1997 | Corder | |
| 5,724,987 A | 3/1998 | Gevins et al. | |
| 5,740,812 A | 4/1998 | Cowan | |
| 5,774,591 A | 6/1998 | Black et al. | |
| 5,983,129 A | 11/1999 | Cowan et al. | |
| 5,983,214 A | 11/1999 | Lang et al. | |
| 5,995,868 A * | 11/1999 | Dorfmeister et al. | 600/544 |
| 6,001,065 A | 12/1999 | DeVito | |
| 6,016,444 A * | 1/2000 | John | 600/544 |
| 6,099,319 A | 8/2000 | Zaltman et al. | |
| 6,117,092 A | 9/2000 | Weinstein et al. | |
| 6,254,536 B1 | 7/2001 | DeVito | |
| 6,259,889 B1 | 7/2001 | LaDue | |
| 6,270,466 B1 | 8/2001 | Weinstein et al. | |
| 6,292,688 B1 | 9/2001 | Patton | |
| 6,309,342 B1 | 10/2001 | Blazey et al. | |
| 6,322,368 B1 | 11/2001 | Young et al. | |
| 6,349,231 B1 | 2/2002 | Musha | |
| 6,422,999 B1 | 7/2002 | Hill | |
| 6,425,764 B1 | 7/2002 | Lamson | |
| 6,434,419 B1 * | 8/2002 | Gevins et al. | 600/544 |
| 6,453,194 B1 | 9/2002 | Hill | |
| 6,481,013 B1 | 11/2002 | Dinwiddie et al. | |
| 6,520,905 B1 | 2/2003 | Surve et al. | |
| 6,585,521 B1 | 7/2003 | Obrador | |
| 6,606,102 B1 | 8/2003 | Odom | |
| 6,609,024 B1 | 8/2003 | Ryu et al. | |
| 6,623,428 B2 | 9/2003 | Miller et al. | |
| 6,626,676 B2 | 9/2003 | Freer | |
| 6,648,822 B2 * | 11/2003 | Hamamoto et al. | 600/300 |
| 6,652,283 B1 | 11/2003 | Van Schaack et al. | |
| 6,656,116 B2 | 12/2003 | Kim et al. | |
| 6,678,866 B1 | 1/2004 | Sugimoto et al. | |
| 6,699,188 B2 | 3/2004 | Wessel | |
| 6,792,304 B1 | 9/2004 | Silberstein | |
| 6,839,682 B1 | 1/2005 | Blume | |
| 6,978,115 B2 | 12/2005 | Whitehurst et al. | |
| 7,035,685 B2 | 4/2006 | Ryu et al. | |
| 7,050,753 B2 | 5/2006 | Knutson | |
| 7,113,916 B1 | 9/2006 | Hill | |
| 7,127,283 B2 | 10/2006 | Kageyama | |
| 7,194,186 B1 | 3/2007 | Strub et al. | |
| 7,246,081 B2 | 7/2007 | Hill | |
| D565,735 S | 4/2008 | Washbon | |
| 7,383,728 B2 | 6/2008 | Noble et al. | |
| 7,627,880 B2 | 12/2009 | Itakura | |
| 7,630,757 B2 * | 12/2009 | Dorfmeister et al. | 600/544 |
| 7,689,272 B2 | 3/2010 | Farwell | |
| 7,716,697 B2 | 5/2010 | Morikawa et al. | |
| 7,739,140 B2 | 6/2010 | Vinson et al. | |
| 7,742,623 B1 | 6/2010 | Moon et al. | |
| 7,751,878 B1 | 7/2010 | Merkle et al. | |
| 7,805,009 B2 | 9/2010 | Everett et al. | |
| 7,853,122 B2 | 12/2010 | Miura et al. | |
| 7,930,199 B1 | 4/2011 | Hill | |
| 7,942,816 B2 * | 5/2011 | Satoh et al. | 600/300 |
| 8,235,725 B1 | 8/2012 | Hill | |
| 8,326,002 B2 | 12/2012 | Hill | |
| 8,600,100 B2 | 12/2013 | Hill | |
| 2001/0016874 A1 | 8/2001 | Ono et al. | |
| 2001/0056225 A1 | 12/2001 | DeVito | |
| 2002/0103429 A1 * | 8/2002 | deCharms | 600/410 |
| 2002/0107454 A1 | 8/2002 | Collura et al. | |
| 2002/0154833 A1 | 10/2002 | Koch et al. | |
| 2002/0182574 A1 | 12/2002 | Freer | |
| 2002/0188216 A1 | 12/2002 | Kayyali et al. | |
| 2003/0003433 A1 | 1/2003 | Carpenter et al. | |
| 2003/0055355 A1 | 3/2003 | Viertio-Oja | |
| 2003/0063780 A1 | 4/2003 | Gutta et al. | |
| 2003/0066071 A1 | 4/2003 | Gutta et al. | |
| 2003/0067486 A1 | 4/2003 | Lee et al. | |
| 2003/0076369 A1 | 4/2003 | Resner | |
| 2003/0081834 A1 | 5/2003 | Philomin et al. | |
| 2003/0093784 A1 | 5/2003 | Dimitrova et al. | |
| 2003/0126593 A1 | 7/2003 | Mault | |
| 2003/0153841 A1 | 8/2003 | Kilborn et al. | |
| 2004/0013398 A1 | 1/2004 | Miura et al. | |
| 2004/0018476 A1 | 1/2004 | Ladue | |
| 2004/0039268 A1 | 2/2004 | Barbour et al. | |
| 2004/0072133 A1 | 4/2004 | Kullok et al. | |
| 2004/0077934 A1 | 4/2004 | Massad | |
| 2004/0088289 A1 | 5/2004 | Xu et al. | |
| 2004/0111033 A1 | 6/2004 | Oung et al. | |
| 2004/0161730 A1 | 8/2004 | Urman | |
| 2004/0193068 A1 * | 9/2004 | Burton et al. | 600/544 |
| 2004/0208496 A1 | 10/2004 | Pilu | |
| 2004/0267141 A1 | 12/2004 | Amano et al. | |
| 2005/0010087 A1 | 1/2005 | Banet | |
| 2005/0010116 A1 | 1/2005 | Korhonen et al. | |
| 2005/0043774 A1 | 2/2005 | Devlin et al. | |
| 2005/0045189 A1 | 3/2005 | Jay | |
| 2005/0066307 A1 | 3/2005 | Patel | |
| 2005/0071865 A1 | 3/2005 | Martins | |
| 2005/0096311 A1 * | 5/2005 | Suffin et al. | 514/217 |
| 2005/0097594 A1 | 5/2005 | O'Donnell et al. | |
| 2005/0113656 A1 | 5/2005 | Chance | |
| 2005/0120372 A1 | 6/2005 | Itakura | |
| 2005/0143629 A1 | 6/2005 | Farwell | |
| 2005/0165285 A1 | 7/2005 | Iliff | |
| 2005/0172311 A1 | 8/2005 | Hjelt et al. | |
| 2005/0223237 A1 | 10/2005 | Barletta et al. | |
| 2005/0289582 A1 | 12/2005 | Tavares et al. | |
| 2006/0010470 A1 | 1/2006 | Kurosaki et al. | |
| 2006/0064037 A1 | 3/2006 | Shalon et al. | |
| 2006/0094970 A1 * | 5/2006 | Drew | 600/509 |
| 2006/0111621 A1 * | 5/2006 | Coppi et al. | 600/300 |
| 2006/0143647 A1 | 6/2006 | Bill | |
| 2006/0217598 A1 | 9/2006 | Miyajima et al. | |
| 2006/0258926 A1 | 11/2006 | Ali et al. | |
| 2006/0265022 A1 | 11/2006 | John et al. | |
| 2006/0277102 A1 | 12/2006 | Agliozzo | |
| 2006/0293608 A1 | 12/2006 | Rothman et al. | |
| 2006/0293921 A1 | 12/2006 | McCarthy et al. | |
| 2007/0031798 A1 | 2/2007 | Gottfried | |
| 2007/0048707 A1 | 3/2007 | Caamano et al. | |
| 2007/0053513 A1 | 3/2007 | Hoffberg | |
| 2007/0055169 A1 | 3/2007 | Lee et al. | |
| 2007/0060830 A1 | 3/2007 | Le et al. | |
| 2007/0060831 A1 | 3/2007 | Le et al. | |
| 2007/0066914 A1 | 3/2007 | Le et al. | |
| 2007/0116037 A1 | 5/2007 | Moore | |
| 2007/0168461 A1 | 7/2007 | Moore | |
| 2007/0173733 A1 * | 7/2007 | Le et al. | 600/544 |
| 2007/0179396 A1 | 8/2007 | Le et al. | |
| 2007/0184420 A1 | 8/2007 | Mathan et al. | |
| 2007/0225585 A1 | 9/2007 | Washbon et al. | |
| 2007/0235716 A1 | 10/2007 | Delic et al. | |
| 2007/0238945 A1 | 10/2007 | Delic et al. | |
| 2007/0249952 A1 | 10/2007 | Rubin et al. | |
| 2007/0265507 A1 | 11/2007 | De Lemos | |
| 2008/0039737 A1 | 2/2008 | Breiter et al. | |
| 2008/0091512 A1 | 4/2008 | Marci et al. | |
| 2008/0144882 A1 | 6/2008 | Leinbach et al. | |
| 2008/0159365 A1 | 7/2008 | Dubocanin et al. | |
| 2008/0161651 A1 * | 7/2008 | Peterson et al. | 600/300 |
| 2008/0162182 A1 * | 7/2008 | Cazares et al. | 705/2 |
| 2008/0177197 A1 | 7/2008 | Lee et al. | |
| 2008/0201731 A1 | 8/2008 | Howcroft | |
| 2008/0211768 A1 | 9/2008 | Breen et al. | |
| 2008/0218472 A1 | 9/2008 | Breen et al. | |
| 2009/0024049 A1 | 1/2009 | Pradeep et al. | |
| 2009/0024447 A1 | 1/2009 | Pradeep et al. | |
| 2009/0024448 A1 | 1/2009 | Pradeep et al. | |
| 2009/0024449 A1 | 1/2009 | Pradeep et al. | |
| 2009/0024475 A1 | 1/2009 | Pradeep et al. | |
| 2009/0025023 A1 | 1/2009 | Pradeep et al. | |
| 2009/0030287 A1 | 1/2009 | Pradeep et al. | |
| 2009/0030303 A1 | 1/2009 | Pradeep et al. | |
| 2009/0030717 A1 | 1/2009 | Pradeep et al. | |
| 2009/0030930 A1 | 1/2009 | Pradeep et al. | |

(56) References Cited

U.S. PATENT DOCUMENTS

| | | |
|---|---|---|
| 2009/0036755 A1 | 2/2009 | Pradeep et al. |
| 2009/0036756 A1 | 2/2009 | Pradeep et al. |
| 2009/0062629 A1 | 3/2009 | Pradeep et al. |
| 2009/0062681 A1 | 3/2009 | Pradeep et al. |
| 2009/0063255 A1 | 3/2009 | Pradeep et al. |
| 2009/0063256 A1 | 3/2009 | Pradeep et al. |
| 2009/0082643 A1 | 3/2009 | Pradeep et al. |
| 2009/0083129 A1 | 3/2009 | Pradeep et al. |
| 2009/0105576 A1 | 4/2009 | Do et al. |
| 2009/0112077 A1 | 4/2009 | Nguyen et al. |
| 2009/0156907 A1* | 6/2009 | Jung et al. ............ 600/300 |
| 2009/0156925 A1 | 6/2009 | Jin et al. |
| 2009/0156955 A1* | 6/2009 | Jung et al. ............ 600/544 |
| 2009/0163777 A1* | 6/2009 | Jung et al. ............ 600/301 |
| 2009/0171164 A1* | 7/2009 | Jung et al. ............ 600/300 |
| 2009/0214060 A1 | 8/2009 | Chuang et al. |
| 2009/0222330 A1 | 9/2009 | Leinbach |
| 2010/0076333 A9 | 3/2010 | Burton et al. |
| 2012/0002848 A1 | 1/2012 | Hill |
| 2012/0046993 A1 | 2/2012 | Hill |
| 2012/0289794 A1* | 11/2012 | Jain et al. ............ 600/301 |
| 2013/0094722 A1 | 4/2013 | Hill |
| 2013/0121591 A1 | 5/2013 | Hill |
| 2014/0039857 A1 | 2/2014 | Hill |
| 2014/0039975 A1 | 2/2014 | Hill |
| 2014/0162225 A1 | 6/2014 | Hill |

FOREIGN PATENT DOCUMENTS

| | | |
|---|---|---|
| EP | 1607842 | 12/2005 |
| JP | 05293172 | 11/1993 |
| JP | 07-329657 | 12/1995 |
| JP | 2002-000577 | 1/2002 |
| JP | 0256500 | 2/2002 |
| JP | 2002-344904 | 11/2002 |
| JP | 2003-016095 | 1/2003 |
| JP | 2003-111106 | 4/2003 |
| JP | 2003-178078 | 6/2003 |
| JP | 2003522580 | 7/2003 |
| JP | 2005084770 | 3/2005 |
| JP | 2006-323547 | 11/2006 |
| KR | 10-2000-0072489 | 12/2000 |
| KR | 10-2001-0104579 | 11/2001 |
| WO | 00/17824 | 3/2000 |
| WO | 01/97070 | 12/2001 |
| WO | 2004100765 | 11/2004 |
| WO | 2006005767 | 1/2006 |
| WO | 2007/019584 | 2/2007 |

OTHER PUBLICATIONS

Form PCT/ISA/210, PCT/US07/15019, "PCT International Search Report," 2 pgs.
Form PCT/ISA/237, PCT/US07/15019, "PCT Written Opinion of the International Searching Authority," 5 pgs.
Form PCT/IB/326, PCT/US07/015019, "Notification Concerning Transmittal of International Preliminary Report on Patentability."
Form PCT/IB/373, PCT/US07/15019, "International Preliminary Report on Patentability."
Form PCT/ISA/220, PCT/US07/14955, "PCT Notification of Transmittal of The International Search Report and the Written Opinion of the International Searching Authority, or the Declaration," 1 pg.
Form PCT/ISA/210, PCT/US07/14955, "PCT International Search Report," 2 pgs.
Form PCT/ISA/237, PCT/US07/14955, "PCT Written Opinion of the International Searching Authority," 6 pgs.
Form PCT/IB/326, PCT/US07/14955, "Notification Concerning Transmittal of International Preliminary Report on Patentability." 1 page.
Form PCT/IB/373, PCT/US07/14955, "International Preliminary Report on Patentability." 1 page.
Form PCT/ISA/220, PCT/US07/16796, "PCT Notification of Transmittal of The International Search Report and the Written Opinion of the International Searching Authority, or the Declaration," 1 pg.
Form PCT/ISA/210, PCT/US07/16796, "PCT International Search Report," 2 pgs.
Form PCT/ISA/237, PCT/US07/16796, "PCT Written Opinion of the International Searching Authority," 6 pgs.
Form PCT/IB/326, PCT/US07/16796, "Notification Concerning Transmittal of International Preliminary Report on Patentability." 1 page.
Form PCT/IB/373, PCT/US07/16796, "International Preliminary Report on Patentability." 1 page.
Form PCT/ISA/220, PCT/US06/31569, "PCT Notification of Transmittal of The International Search Report and the Written Opinion of the International Searching Authority, or the Declaration," 1 pg.
Form PCT/ISA/210, PCT/US06/31569, "PCT International Search Report," 3 pgs.
Form PCT/ISA/237, PCT/US06/31569, "PCT Written Opinion of the International Searching Authority," 6 pgs.
Form PCT/IB/326, PCT/US06/31569, "Notification Concerning Transmittal of International Preliminary Report on Patentability." 1 page.
Form PCT/IB/373, PCT/US06/31569, "International Preliminary Report on Patentability." 1 page.
Form PCT/ISA/220, PCT/US07/20714, "PCT Notification of Transmittal of The International Search Report and the Written Opinion of the International Searching Authority, or the Declaration," 1 pg.
Form PCT/ISA/210, PCT/US07/20714, "PCT International Search Report," 2 pgs.
Form PCT/ISA/237, PCT/US07/20714, "PCT Written Opinion of the International Searching Authority," 6 pgs.
Form PCT/IB/326, PCT/US07/20714, "Notification Concerning Transmittal of International Preliminary Report on Patentability." 1 page.
Form PCT/IB/373, PCT/US07/20714, "International Preliminary Report on Patentability." 1 page.
Form PCT/ISA/220, PCT/US07/17764, "PCT Notification of Transmittal of The International Search Report and the Written Opinion of the International Searching Authority, or the Declaration," 1 pg.
Form PCT/ISA/210, PCT/US07/17764, "PCT International Search Report," 2 pgs.
Form PCT/ISA/237, PCT/US07/17764, "PCT Written Opinion of the International Searching Authority," 7 pgs.
Form PCT/IB/326, PCT/US07/17764, "Notification Concerning Transmittal of International Preliminary Report on Patentability." 1 page.
Form PCT/IB/373, PCT/US07/17764, "International Preliminary Report on Patentability." 1 page.
Form PCT/ISA/220, PCT/US07/20713, "PCT Notification of Transmittal of The International Search Report and the Written Opinion of the International Searching Authority, or the Declaration," 1 pg.
Form PCT/ISA/210, PCT/US07/20713, "PCT International Search Report," 2 pgs.
Form PCT/ISA/237, PCT/US07/20713, "PCT Written Opinion of the International Searching Authority," 5 pgs.
Form PCT/IB/326, PCT/US07/20713, "Notification Concerning Transmittal of International Preliminary Report on Patentability." 1 page.
Form PCT/IB/373, PCT/US07/20713, "International Preliminary Report on Patentability." 1 page.
Form PCT/ISA/220, PCT/US08/09110, "PCT Notification of Transmittal of The International Search Report and the Written Opinion of the International Searching Authority, or the Declaration," 1 pg.
Form PCT/ISA/210, PCT/US08/09110, "PCT International Search Report," 3 pgs.
Form PCT/ISA/237, PCT/US08/09110, "PCT Written Opinion of the International Searching Authority," 4 pgs.
Form PCT/ISA/220, PCT/US08/75640, "PCT Notification of Transmittal of The International Search Report and the Written Opinion of the International Searching Authority, or the Declaration," 1 pg.
Form PCT/ISA/210, PCT/US08/75640, "PCT International Search Report," 2 pgs.
Form PCT/ISA/237, PCT/US08/75640, "PCT Written Opinion of the International Searching Authority," 3 pgs.

(56) References Cited

OTHER PUBLICATIONS

Form PCT/ISA/220, PCT/US08/78633, "PCT Notification of Transmittal of The International Search Report and the Written Opinion of the International Searching Authority, or the Declaration," 1 pg.
Form PCT/ISA/210, PCT/US08/78633, "PCT International Search Report," 2 pgs.
Form PCT/ISA/237, PCT/US08/78633, "PCT Written Opinion of the International Searching Authority," 6 pgs.
Form PCT/ISA/220, PCT/US08/82147, "PCT Notification of Transmittal of The International Search Report and the Written Opinion of the International Searching Authority, or the Declaration," 1 pg.
Form PCT/ISA/210, PCT/US08/82147, "PCT International Search Report," 2 pgs.
Form PCT/ISA/237, PCT/US08/82147, "PCT Written Opinion of the International Searching Authority," 13 pgs.
Form PCT/ISA/220, PCT/US08/82149, "PCT Notification of Transmittal of The International Search Report and the Written Opinion of the International Searching Authority, or the Declaration," 1 pg.
Form PCT/ISA/210, PCT/US08/82149, "PCT International Search Report," 2 pgs.
Form PCT/ISA/237, PCT/US08/82149, "PCT Written Opinion of the International Searching Authority," 14 pgs.
Form PCT/ISA/220, PCT/US08/75651, "PCT Notification of Transmittal of The International Search Report and the Written Opinion of the International Searching Authority, or the Declaration," 1 pg.
Form PCT/ISA/210, PCT/US08/75651, "PCT International Search Report," 2 pgs.
Form PCT/ISA/237, PCT/US08/75651, "PCT Written Opinion of the International Searching Authority," 9 pgs.
Form PCT/ISA/220, PCT/US08/85723, "PCT Notification of Transmittal of The International Search Report and the Written Opinion of the International Searching Authority, or the Declaration," 1 pg.
Form PCT/ISA/210, PCT/US08/85723, "PCT International Search Report," 2 pgs.
Form PCT/ISA/237, PCT/US08/85723, "PCT Written Opinion of the International Searching Authority," 7 pgs.
Form PCT/ISA/220, PCT/US08/85203, "PCT Notification of Transmittal of The International Search Report and the Written Opinion of the International Searching Authority, or the Declaration," 1 pg.
Form PCT/ISA/210, PCT/US08/85203, "PCT International Search Report," 2 pgs.
Form PCT/ISA/237, PCT/US08/85203, "PCT Written Opinion of the International Searching Authority," 6 pgs.
Form PCT/ISA/220, PCT/US08/75649, "PCT Notification of Transmittal of The International Search Report and the Written Opinion of the International Searching Authority, or the Declaration," 1 pg.
Form PCT/ISA/210, PCT/US08/75649, "PCT International Search Report," 3 pgs.
Form PCT/ISA/237, PCT/US08/75649, "PCT Written Opinion of the International Searching Authority," 5 pgs.
Technology Platform: SmartShirt + Eye-Tracking Innerscope Research, Mar. 2007.
Egner, Tobias; Emilie Strawson, and John H. Gruzelier, "EEG Signature and Phenomenology of Alpha/theta Neurofeedback Training Versus Mock Feedback." Applied Psychophysiology and Biofeedback. vol. 27, No. 4. Dec. 2002.
Clarke, Adam R. et al., EEG Analysis of Children with Attention-Deficit/Hyperactivity Disorder and Comorbid Reading Disabilities, Journal of Learning Disabilities, vol. 35, No. 3, (May-Jun. 2002), pp. 276-285.
Carter, R., " Mapping the Mind" 1998 p. 182 University of California Press, Berkley.
Harmony et al. (2004) Specific EEG frequencies signal general common cognitive processes as well as specific tasks processes in man. Int. Journal of Psychophysiology 53(3): 207-16.
Klimesch, W., Schimke, H., Schwaiger, J. (1994) Episodic and semantic memory: an analysis in the EEG theta and alpha band. Electroencephalography Clinical Neurophysiology.
Mizuhara, H.,Wang LQ, Kobayashi, K., Yamaguchi, Y., (2004) A long range cortical network emerging with theta oscillation in mental task. Neuroreport 15(8): 1233-1238.
Selden, G (1981) "Machines that Read Minds." Science Digest, October.
Willis, M. & Hodson, V.; Discover Your Child's Learning Style: Children Learn in Unique Ways—Here's the Key to Every Child's Learning Success, Prime Publishing. Roseville, CA.
Wise, A (1996) The High Performance Mind, Mastering Brainwaves for Insight, Healing and Creativity. G.P. Putnam's Son, New York. pp. 13-15; 20-22; 143-156.
Wise, A (1996) The High Performance Mind, Mastering Brainwaves for Insight, Healing and Creativity. G.P. Putnam's Son, New York. pp. 156-158; 165-170; 186-187, 189-192.
El-Bab, M. (2001) Cognitive event related potentials during a learning task. Doctoral Dissertation, Faculty of Medicine, University of Southampton, UK.
Gevins et al. (1997) High resolution EEG mapping of cortical activation related to a working memory, Cereb Cortex. 7: 374-385.
Hughes, J.R. & John, E.R. (1999) Conventional and Quantitative Electroencephalography in Psychiatry. Journal of Neuropsychiatry and Clinical Neurosciences. vol. 11(2): 190-208.
Coan, J. A, et al., "Voluntary Facial Expression and Hemispheric Asymmetry Over the Frontal Cortex," Psychophysiology, 38 (Nov. 2001), pp. 912-925, 14 pages.
Summons to Attend Oral Proceedings Pursuant to Rule 115(1) EPC, issued by the European Patent Office in connection with European Patent Application No. 07796518.4 on Sep. 4, 2014, 7 pages.
Notification of the Second Office Action, issued by the State Intellectual Property Office of the P.R. China, in connection with Chinese Patent Application No. 201210063607.5, on Aug. 28, 2014, 9 pages.
Office Action, issued by the United States Patent and Trademark Office in connection with U.S. Appl. No. 12/206,676, on Oct. 2, 2014, 13 pages.
Notification of Reason(s) for Rejection, issued by the Japanese Intellectual Property Office in connection with Japanese Patent Application No. JP2009552656, on Aug. 27, 2014, 13 pages.
Interrogative Statement, English Language, issued by the Intellectual Property Office of Japan, in connection with Japanese application No. 2009-552656, on Oct. 25, 2013, 4 pages.
European Office Action, issued by the European Patent Office in connection with European Patent Application No. 07796518.4, on Sep. 13, 2013, 7 pages.
European Office Action, issued by the European Patent Office in connection with European Patent Application No. 07838838.6, on Oct. 23, 2013, 4 pages.
Office Action, issued by the United States Patent and Trademark Office in connection with U.S. Appl. No. 13/553,515 on Jul. 17, 2013, 12 pages.
First Office Action and Search Report, with English Language Version, issued by the State Intellectual Property Office of the Peoples' Republic of China, in connection with Chinese Patent Application No. 201210244954.8, on Jan. 2, 2014, 25 pages.
Notification of Reasons(s) for Rejection, issued by the Japanese Intellectual Property Office in connection with Japanese Patent Application No. 2012-152836, Jan. 14, 2014, 5 pages.
Notice of Allowance and Fee(s) Due, issued by the United States Patent and Trademark Office in connection with U.S. Appl. No. 11/845,993, on Feb. 19, 2014, 10 pages.
European Office Action, issued by the European Patent Office in connection with European Patent Application 07 852 430.3, on Feb. 3, 2014, 3 pages.
Notification of Grant of Patent Right for Invention, issued by the State Intellectual Property Office of the P.R. China, in connection with Chinese Patent Application No. 200780052869.9, on Aug. 31, 2012, 1 page.
Notification of the Third Office Action, issued by the State Intellectual Property Office of the P.R. China, in connection with Chinese Patent Application No. 200780052868.4, on Aug. 9, 2012, 7 pages.
Notification of the Second Office Action, issued by the State Intellectual Property Office of the P.R. China, in connection with Chinese Patent Application No. 200780052879.2, on May 4, 2012, 11 pages.

(56) References Cited

OTHER PUBLICATIONS

Notification of the Third Office Action, issued by the State Intellectual Property Office of the P.R. China, in connection with Chinese Patent Application No. 200680031159.3, on Mar. 28, 2012, 6 pages.
Notification of the Second Office Action, issued by the State Intellectual Property Office of the P.R. China, in connection with Chinese Patent Application No. 200680031159.3, on Oct. 19, 2011, 8 pages.
Notification of the Third Office Action, issued by the State Intellectual Property Office of the P.R. China, in connection with Chinese Patent Application No. 200780052879.2, on Dec. 31, 2012, 10 pages.
European Office Action, issued by the European Patent Office in connection with European Patent Application 07 838 838.6, on Sep. 5, 2012, 5 pages.
Supplemental European Search Report, issued by the European Patent Office in connection with European Patent Application No. 07796518.4, on Jul. 11, 2012, 8 pages.
European Office Action, issued by the European Patent Office in connection with European Patent Application No. 07 810 808.1, on Dec. 1, 2011, 6 pages.
Supplemental European Search Report, issued by the European Patent Office in connection with European Patent Appliation No. 06824810.3, on Nov. 22, 2011, 14 pages.
European Office Action, issued by the European Patent Office in connection with European Patent Application No. 07 852 430.3, on Feb. 6, 2013, 5 pages.
European Office Action, issued by the European Patent Office in connection with European Patent Application No. 07 852 430.3, on Mar. 6, 2012, 5 pages.
Supplemental European Search Report, issued by the European Patent Office in connection with European Patent Application No. 07811241.4, on Feb. 14, 2012, 6 pages.
European Office Action, issued by the European Patent Office in connection with European Patent Application No. 07 838 838.6, on Sep. 23, 2011, 4 pages.
Supplemental European Search Report, issued by the European Patent Office in connection with European Patent Application No. 06824810.3, on Nov. 3, 2011, 13 pages.
Supplemental European Search Report, issued by the European Patent Office in connection with European Patent Application No. 07796518.4, on Jul. 30, 2012, 9 pages.
Notification of Reason(s) for Rejection, issued by the Japanese Intellectual Property Office in connection with Japanese Patent Application No. 2009-552658, on Apr. 19, 2012, 2 pages.
Notification of Reason(s) for Rejection, issued by the Japanese Intellectual Property Office in connection with Japanese Patent Application No. 2009-552657, on May 2, 2012, 5 pages.
Notification of Reason(s) for Rejection, issued by the Japanese Intellectual Property Office in connection with Japanese Patent Application No. 2009-552656, on Mar. 30, 2012, 3 pages.
Notification of Reasons(s) for Rejection, issued by the Japanese Intellectual Property Office in connection with Japanese Patent Application No. 2008-529085, Nov. 29, 2011, 2 pages.
Notification of Reasons(s) for Rejection, issued by the Japanese Intellectual Property Office in connection with Japanese Patent Application No. 2009-552661, Nov. 13, 2012, 3 pages.
Notification of Reasons(s) for Rejection, issued by the Japanese Intellectual Property Office in connection with Japanese Patent Application No. 2009-552659, Nov. 16, 2012, 4 pages.
Notification of Reasons(s) for Rejection, issued by the Japanese Intellectual Property Office in connection with Japanese Patent Application No. 2009-552660, Nov. 16, 2012, 3 pages.
Notice of Allowance and Fee(s) Due, issued by the United States Patent and Trademark Office in connection with U.S. Appl. No. 11/804,517, on Mar. 21, 2012, 8 pages.
Final Rejection, issued by the United States Patent and Trademark Office in connection with U.S. Appl. No. 11/804,517, on Sep. 1, 2011, 11 pages.
Office Action, issued by the United States Patent and Trademark Office in connection with U.S. Appl. No. 11/804,517, on Feb. 3, 2011, 15 pages.
Final Rejection, issued by the United States Patent and Trademark Office in connection with U.S. Appl. No. 11/804,517, on Jun. 23, 2010, 14 pages.
Office Action, issued by the United States Patent and Trademark Office in connection with U.S. Appl. No. 11/804,517, on Sep. 17, 2009, 15 pages.
Office Action, issued by the United States Patent and Trademark Office in connection with U.S. Appl. No. 11/804,555, on Mar. 15, 2012, 15 pages.
Final Rejection, issued by the United States Patent and Trademark Office in connection with U.S. Appl. No. 11/804,555, on Oct. 9, 2012, 11 pages.
Final Rejection, issued by the United States Patent and Trademark Office in connection with U.S. Appl. No. 11/804,555, on Jul. 21, 2010, 14 pages.
Office Action, issued by the United States Patent and Trademark Office in connection with U.S. Appl. No. 11/804,555, on Oct. 1, 2009, 17 pages.
Office Action, issued by the United States Patent and Trademark Office in connection with U.S. Appl. No. 11/779,814, on Feb. 13, 2012, 19 pages.
Final Rejection, issued by the United States Patent and Trademark Office in connection with U.S. Appl. No. 11/779,814, on Jun. 28, 2012, 18 pages.
Final Rejection, issued by the United States Patent and Trademark Office in connection with U.S. Appl. No. 11/779,814, on Jun. 18, 2010, 24 pages.
Office Action, issued by the United States Patent and Trademark Office in connection with U.S. Appl. No. 11/779,814, on Oct. 5, 2009, 24 pages.
Final Rejection, issued by the United States Patent and Trademark Office in connection with U.S. Appl. No. 11/500,678, on Dec. 8, 2010, 9 pages.
Office Action, issued by the United States Patent and Trademark Office in connection with U.S. Appl. No. 11/500,678, on Mar. 17, 2010, 10 pages.
Office Action, issued by the United States Patent and Trademark Office in connection with U.S. Appl. No. 11/500,678, on Sep. 3, 2008, 12 pages.
Final Rejection, issued by the United States Patent and Trademark Office in connection with U.S. Appl. No. 11/500,678, on , Jun. 9, 2009, 11 pages.
Final Rejection, issued by the United States Patent and Trademark Office in connection with U.S. Appl. No. 11/845,993, on Apr. 24, 2012, 8 pages.
Advisory Action, issued by the United States Patent and Trademark Office in connection with U.S. Appl. No. 11/845,993, on Jul. 20, 2012, 4 pages.
Office Action, issued by the United States Patent and Trademark Office in connection with U.S. Appl. No. 11/845,993, Aug. 4, 2011, 12 pages.
Final Rejection, issued by the United States Patent and Trademark Office in connection with U.S. Appl. No. 11/835,634, on Apr. 25, 2012, 23 pages.
Office Action, issued by the United States Patent and Trademark Office in connection with U.S. Appl. No. 11/835,634, on Sep. 1, 2011, 16 pages.
Office Action, issued by the United States Patent and Trademark Office in connection with U.S. Appl. No. 11/835,634, on Feb. 26, 2013, 24, pages.
Final Rejection, issued by the United States Patent and Trademark Office in connection with U.S. Appl. No. 12/206,676, on Mar. 6, 2012, 9 pages.
Office Action, issued by the United States Patent and Trademark Office in connection with U.S. Appl. No. 12/206,676, on May 10, 2011, 9 pages.
Final Rejection, issued by the United States Patent and Trademark Office in connection with U.S. Appl. No. 12/206,702, on Jun. 3, 2010, 8 pages.
Office Action, issued by the United States Patent and Trademark Office in connection with U.S. Appl. No. 12/206,702, on May 28, 2009, 8 pages.

(56) References Cited

OTHER PUBLICATIONS

Restriction and/or Election Requirement, issued by the United States Patent and Trademark Office in connection with U.S. Appl. No. 11/846,068, on Feb. 21, 2012, 6 pages.
Office Action, issued by the United States Patent and Trademark Office in connection with U.S. Appl. No. 11/846,068, on Apr. 27, 2012, 9 pages.
Notice of Allowance and Fee(s) Due, issued by the United States Patent and Trademark Office in connection with U.S. Appl. No. 11/846,068, on Dec. 26, 2012, 9 pages.
Office Action, issued by the United States Patent and Trademark Office in connection with U.S. Appl. No. 12/835,714, on Jan. 22, 2013, 34 pages.
Adamic et al., "The political blogosphere and the 2004 U.S. election: Divided they blog," Proceedings WWW-2005 2nd Annual Workshop on the Weblogging Ecosystem, 2005, Chiba, Japan, 16 pages.
Adar et al., "Implicit structure and the dynamics of blogspace," Proceedings WWW-2004 Workshop on the Weblogging Ecosystem, 2004, New York, NY, 8 pages.
Aliod et al., "A Real World Implementation of Answer Extraction," Department of Computer Science, University of Zurich, Winterthurerstr. 190, CH-8057 Zurich, Switzerland, 6 pages.
Bishop, Mike, "Arrow Question/Answering Systems," Language Computer Corporation, 1999, 3 pages.
Bizrate, archived version of www.bizrate.com, Jan. 1999, 22 pages.
Blum, "Empirical Support for Winnow and Weighted-Majority Algorithms: Results on a Calendar Scheduling Domain," in Machine Learning, vol. 26, Kluwer Academic Publishers, Boston, USA, 1997, 19 pages.
Bournellis, Cynthia, "Tracking the hits on Web Sites," Communications International: vol. 22, Issue 9, London, Sep. 1995, 3 pages.
Chaum et al., "A Secure and Privacy-Protecting Protocol for Transmitting Personal Information Between Organizations," A.M. Odlyzko (Ed.): Advances in Cryptology, CRYPTO '86, LNCS 263, 1987, 51 pages.
Chaum, David L., "Untraceable Electronic Mail, Return Addresses, and Digital Pseudonymns," Communication of the ACM, vol. 24, No. 2, 1981, 5 pages.
Cohen, William W., "Data Integration using similarity joins and a word-based information representation language," ACM Transactions on Information Systems, vol. 18, No. 3, Jul. 2000, 34 pages.
Cohn et al., "Active Learning with Statistical Models," Journal of Artificial Intelligence Research 4, A1 Access Foundation and Morgan Kaufmann Publishers, USA, 1996, 17 pages.
Dagan et al., "Mistake-Driven Learning in Text Categorization," in EMNLP '97, $2^{nd}$ Conference on Empirical Methods in Natural Language Processing, 1997, 9 pages.
Delahaye Group, "Delahaye Group to Offer Nets Bench: High Level Web-Site Qualitative Analysis and Reporting; NetBench Builds on Systems provided by I/PRO and Internet Media Services," 1995 Business Wire, Inc., May 31, 1995, 3 pages.
Dialogic, www.dialogic.com as archived on May 12, 2000, 34 pages.
Dillon et al., "Marketing research in a Marketing Environment," Times Mirror/Mosby College, USA, 1987, 5 pages.
Ewatch, eWatch's archived web site retrieved from [URL: http://web.archive.org/web/19980522190526/wwww.ewatch.com] on Sep. 8, 2004, archived May 22, 1998, 50 pages.
Egner et al., "EEG Signature and Phenomenology of Alpha/theta Neurofeedback Training Versus Mock Feedback," Applied Psychophysiology and Biofeedback, vol. 27, No. 4, Dec. 2002, 10 pages.
Farber, Dave, "IP: eWatch and Cybersleuth," retrieved from [URL: http://www.interesting-people.org/archives/interesting-people/200006/msg00090.html] Jun. 29, 2000, 4 pages.
Freund et al., "Selective Sampling Using the Query by Committee Algorithm," Machine Learning 28 Kluwer Academic Publishers, The Netherlands, 1997, 36 pages.
Glance et al., "Analyzing online disussion for marketing intelligence," Proceedings WWW-2005 2nd Annual Workshop on the Weblogging Ecosystem, Chiba, Japan, 2005, 2 pages.
Glance et al., "Deriving marketing intelligence from online discussion," 11th ACM SIGKDD International Conference on Knowledge Discovery and Data Mining, Chicago, IL, Aug. 21-24, 2005, 10 pages.
Grefenstette et al., "Validating the Coverage of Lexical Resources for Affect Analysis and Automatically Classifying New Words along Semantic Axes," Chapter X, 3, Mar. 2004, 16 pages.
Harabagiu, Sanda M., "An Intelligent System for Question Answering," University of Southern California; Modlovan, Dan, Southern Methodist University, 1996, 5 pages.
Harabagiu, Sanda M., "Experiments with Open-Domain Textual Question Answering," Department of Computer Science and Engineering at Southern Methodist Universtity, 2000, 7 pages.
Harabagiu, Sanda M., "Mining Textual Answers with Knowledge-Based Indicators," Department of Computer Science and Engineering at Southern Methodist University, 2000, 5 pages.
Housley et al., "Internet X.509 Public Key Infrastructure Certificate and CRL Profile," Network Working Group Request for Comments: 2459, Jan. 1999, 121 pages.
Joachims, Thorsten, "Text Categorization with Support Vector Machines: Learning with Many Relevant Features," in Machine Learning: ECML-98, Tenth European Conference on Machine Learning, 1998, 7 pages.
Kahn et al., "Categorizing Web Documents using Competitive Learning: An ingrediant of a Personal Adaptive Agent," IEEE 1997, 4 pages.
Katz, Boris, "From Sentence Processing to Information Access on the World Wide Web," MIT Artificial Intelligence Laboratory, Feb. 27, 1997, 20 pages.
Kleppner, "Advertising Procedure," 6th edition, 1977, Prentice-Hall, Inc., Englewood Cliffs, NJ, p. 492, 3 pages.
Kotler, "Marketing Management," PrenticeHall International Inc., Upper Saddle River, NJ, 1997, 10 pages.
Klimesch, "EEG alpha and theta oscillations reflect cognitive and memory performance: a review and analysis," Brain Research Reviews, vol. 29, 1999, 27 pages.
Lenz et al., "Question answering with Textual CBR," Department of Computer Science, Humboldt University Berlin, D-10099 Berlin, 1998, 12 pages.
Littlestone, Nick, "Learning Quickly when Irrelevant Attributes Abound: A New Linear-threshold Algorithm," in Machine Learning, vol. 2, Kluwer Academic Publishers, Boston, MA, 1988, 34 pages.
Marlow, "Audience, structure and authority in the weblog community," International Communication Association Conference, MIT Media Laboratory, New Orleans, LA 2004, 9 pages.
McCallum et al., "Text Classification by Bootstrapping with the Keywords, EM and Shrinkage," Just Research and Carnegie Mellon University, Pittsburgh, PA, circa 1999, 7 pages.
McLachlan et al., "The EM Algorithm and Extensions," John Wiley & Sons, Inc., New York, NY, 1997, 301 pages.
Moldovan et al., "LASSO: A Tool for Surfing the Answer Net," Department of Computer Science and Engineering at Southern Methodist University, 1999, 9 pages.
Nakashima et al., "Information Filtering for the Newspaper," IEEE 1997, 4 pages.
Nanno et al., "Automatic collection and monitoring of Japanese Weblogs," Proceedings WWW-2004 Workshop on the weblogging Ecosystem, 2004, New York, NY, 7 pages.
Netcurrent, NetCurrent's web site, http://web.archive.org/web/20000622024845/www.netcurrents.com, retrieved on Jan. 17, 2005, archived on Jun. 22, 2000 and Sep. 18, 2000, 17 pages.
Pang et al., "Thumbs up? Sentiment Classification using Machine Learning Techniques," in Proceedings of EMNLP 2002, 8 pages.
Reguly, "Caveat Emptor Rules on the Internet," The Globe and Mail (Canada): Report on Business Column, Apr. 10, 1999, 2 pages.
Reinartz, "Customer Lifetime Value Analysis: An Integrated Empirical Framework for Measurement and Explanation," dissertation: Apr. 1999, 68 pages.
Schmidt et al., "Frontal brain electrical activity (EEG) distinguishes valence and intensity of musical emotions," Cognition and Emotion, vol. 15 (4), Psychology Press Ltd, 2001, 14 pages.

(56) References Cited

OTHER PUBLICATIONS

Sammler, "Music and emotion: Electrophysiological correlates of the processing of pleasant and unpleasant music," Psychophysiology, vol. 44, Blackwell Publiching Inc., 2007, 12 pages.
Soderland et al., "Customer Satisfaction and Links to Customer Profitability: An Empirical Examination of the Association Between Attitudes and Behavior," SSE/EFI Working Paper Series in Business Administration, Jan. 1999, 22 pages.
Thomas, "International Marketing," International Textbook Company, Scranton, PA 1971, 3 pages.
Trigaux, Robert, "Cyberwar Erupts Over Free Speech Across Florida, Nation," Knight-Ridder Tribune Business News, May 29, 2000, 4 pages.
Tull et al., "Marketing Research Measurement and Method," MacMillan Publishing Company, New York, NY, 1984, 9 pages.
Voorhees, Ellen M., "The TREC-8 Question Answering Track Report," National Institute of Standards and Technology, 1999, 6 pages.
Wiebe et al., "Identifying Collocations for Recognizing Opinions," in proceedings of ACL/EACL '01 Workshop on Collocation, Toulouse, France, Apr. 9, 2001, 9 pages.
Word of Mouth Research Case Study, "The Trans Fat Issue, Analysis of online consumer conversation to understand how the Oreo lawsuit impacted word-of-mouth on trans fats," Aug. 16, 2004, 35 pages.
Yang, "An Evaluation of Statistical Approaches to Text Categorization," Information Retrieval 1 (1/2) Apr. 10, 1999, 12 pages.
Zagat, www.zagat.com, archived on Apr. 29, 1999, 33 pages.
Zagat, www.zagat.com, archived version of p. 34, Feb. 1999, 1 page.
Notice of Allowance and Fee(s) Due, issued by the United States Patent and Trademark Office in connection with U.S. Appl. No. 11/804,555, on Mar. 3, 2014, 7 pages.
Notification of Reasons(s) for Rejection, issued by the Japanese Intellectual Property Office in connection with Japanese Patent Application No. 2009-552660 Jan. 21, 2014, 4 pages.
Office Action, issued by the United States Patent and Trademark Office in connection with U.S. Appl. No. 13/553,515, on Jun. 20, 2014, 12 pages.
Notification of the Second Office Action, issued by the State Intellectual Property Office of the P.R. China, in connection with Chinese Patent Application No. 201210244954.8 on Jul. 10, 2014, 26 pages.
Notice for Reasons for Rejection, English Language, issued by the Intellectual Property Office of Japan, in connection with Japanese application No. 2009-552661, on Apr. 24, 2013, 2 pages.
Decision of Rejection, English Language, issued by the State Intellectual Property Office of the P.R. China, in connection with Chinese application No. 2007800528791, on May 29, 2013, 11 pages.
Decision of Rejection, Chinese Language, issued by the State Intellectual Property Office of the P.R. China, in connection with Chinese application No. 2007800528791, on May 29, 2013, 7 pages.
Final Office Action, issued by the United States Patent and Trademark Office in connection with U.S. Appl. No. 11/835,634 on Jun. 20, 2013, 23 pages.
Final Decision of Rejection, English Language, issued by the Japanese Intellectual Property Office in connection with Japanese application No. 2009-552656, on Jan. 21, 2013, 3 pages.

Notice of Reason for Rejection, English Language, issued by the Japanese Intellectual Property Office in connection with Japanese application No. 2009-552660, on Mar. 13, 2013, 3 pages.
Notice of Panel Decision from Pre-Appeal Brief Review, issued by the United States Patent and Trademark Office in connection with U.S. Appl. No. 11/804,555, on Mar. 25, 2013, 2 pages.
Advisory Action, issued by the United States Patent and Trademark Office in connection with U.S. Appl. No. 11/804,555, on Mar. 6, 2013, 3 pages.
Decision of Rejection, English Language, issued by the State Intellectual Property Office of the P.R. China, in connection with Chinese application No. 201210063607.5, on Nov. 19, 2013, 10 pages.
Decision of Rejection, Chinese Language, issued by the State Intellectual Property Office of the P.R. China, in connection with Chinese application No. 201210063607.5, on Nov. 19, 2013, 6 pages.
Final Office Action, issued by the United States Patent and Trademark Office in connection with U.S. Appl. No. 13/553,515 on Jan. 9, 2014, 13 pages.
Non Final Office Action, issued by the United States Patent and Trademark Office in connection with U.S. Appl. No. 11/500,678 on Mar. 18, 2014, 10 pages.
European Office Action, issued by the European Patent Office in connection with European Patent Application No. 07 838838.6 on Mar. 12, 2014, 3 pages.
Final Rejection, issued by the United States Patent and Trademark Office in connection with U.S. Appl. No. 12/206,676, on Jun. 19, 2015, 16 pages.
Final Office Action, issued by the United States Patent and Trademark Office in connection with U.S. Appl. No. 11/500,678 on Nov. 12, 2014, 17 pages.
Notification of Grant of Patent Right for Invention, issued by the State Intellectual Property Office of the P.R. China, in connection with Chinese Patent Application No. 201210244954.8 on Dec. 16, 2014, 6 pages.
Notification of Reexamination, issued by the State Intellectual Property Office of the P.R. China, in connection with Chinese Patent Application No. 200780052879.2, on Feb. 4, 2015, 21 pages.
European Office Action, issued by the European Patent Office in connection with European Patent Application 07838838.6, on Feb. 23, 2015, 3 pages.
Notice of Allowance and Fee(s) Due, issued by the United States Patent and Trademark Office in connection with U.S. Appl. No. 11/500,678, on Mar. 24, 2015, 10 pages.
European Decision and Minutes, issued by the European Patent Office in connection with European Patent Application 07796518.4 on Mar. 12 and 13, 2015, 65 pages.
Notification on Grant of Patent Right for Invention, issued by the State Intellectual Property Office of the P.R. China, in connection with Chinese Patent Application No. 201210063607.5, on Mar. 31, 2015, 4 pages.
The State Intellectul Property Office of China, "Notification of Reexamination", issued in connection with application No. 200780052879.2, on Jul. 1, 2015, 12 pages. (English translation provided).

\* cited by examiner

APPARATUS AND METHOD FOR OBJECTIVELY DETERMINING HUMAN RESPONSE TO MEDIA

BACKGROUND

Commercial media products, such as video games, television programs, movies, books and advertising, are often very expensive to produce. Such media includes events which are designed to provoke a reaction from a user, such as fear or excitement for example, while the user is using or experiencing the media. Since the effectiveness of the events can be directly related to the success of the media product, it is therefore important for the producers of the media to maximize the effectiveness of the events.

In order to maximize the effectiveness of the events, the producer must have a way to objectively determine a level of effectiveness of the events. However many methods used only provide a subjective indication of the effectiveness of the media. Some developers of video games, for instance, have dedicated testing practices for determining marketability or the prospective chances of success of the developer's games. Many of these testing practices involve user's relating feedback about the media. For instance, game developers may have a number of people play their game and then fill out a survey which questions the players about the game. These surveys attempt to elicit responses from the players regarding gameplay design issues and ideas of fun. However, players introduce biases which make the feedback subjective. The surveys also rely on the player's willingness and ability to provide feedback. Also, the surveys cannot address the full scope of the game experience since that would require the player to remember each event in the media and the player's reaction related to each of the events.

Other types of subjective feedback involve focus groups where a group of individuals discuss the game design. However, focus groups include the occurrence of groupthink, where the members of the group try to achieve consensus rather than open discussion on the effectiveness or merits of the media. Also, in these situations a single member of the group can dominate the discussion and the opinion, thereby limiting the range of constructive feedback. Finally, it is difficult to extract useful insights for media design because discussions often center on abstract concepts rather than specific events in the media. The same subjective measures are used in advertising, TV, movie, books and production of other media.

Some producers of media have turned to the use of psychophysiology devices in order to have a more objective determination of the effectiveness of the media. Psychophysiology involves identifying and/or using a connection between psychology and physiology. Psychophysiology can be used to objectively determine a person's emotions, feelings and thoughts related to an event in media based on the person's physiological response to the event. Prior psychophysiology devices have had only limited success in the area of media analysis because of problems associated with sensors of the devices and costs, among other reasons.

One of the problems associated with prior psychophysiology devices is that the measurement station hardware is bulky and extremely expensive. The measurement station requires tens of thousands of dollars in sensing equipment, data recorders and computer interfaces. The measurement station also requires the attention of skilled personnel for set up, operation and maintenance. These measurement stations include wierd sensors that must be attached or glued at various locations across the person's body to detect phsiological responses to the media. These wired sensors are susceptible to data errors from movement and other non-physiological related sources, such as lighting. Accordingly, the person must remain as motionless as possible during a session or test to avoid causing data errors which could render the test useless. Because the person must remain as motionless as possible during the test, these tests are typically short, simple, and do not capture a full game experience in the instance where the media is a video game.

Another problem encountered with the use of prior psychophysiology sensor devices is that errors produced by these devices are difficult or impossible to determine. Errors introduced by outside influences may be interpreted as physiological responses to the media. A skilled operator often must subjectively determine whether the response was generated by a physiological response to the media or if the response is a result of errors in the system.

In addition, it is unclear whether these tests provide actionable information for game, movie, television, advertising and other design because a gap exists between these tests and insights relating to the media. This gap may at least partially be a result of the narrow scope of these previous tests which limits the amount and quality of data gathered. However, another reason for the limited benefit of these tests is that techniques have not previously been developed to translate the data gathered by the measurement station into gameplay design terms and issues.

The foregoing examples of the related art and limitations related therewith are intended to be illustrative and not exclusive. Other limitations of the related art will become apparent to those of skill in the art upon reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In general, a media analysis device and method are described for use in objectively determining a user's emotional response to events in media. In one example, a method for objectively determining a response of a user to at least one event in media experienced by the user is disclosed. In the method a first physiological response is detecting in the user while the user experiences the event and a first physiological response signal is generated in response thereto. A second, different physiological response is also detected in the user while the user experiences the event and a second physiological response signal is generated in response thereto. A scaling factor is applied to a selected one of the physiological response signals. The first and second physiological response signals are used to determine an emotional response of the user to the event. The scaling factor is changed depending on a characteristic of at least one of the first and second physiological response signals.

Another disclosure involves objectively determining a response of a user to at least one event in media experienced by the user where a brain wave is detected from the user's brain while the user experiences the event and a brainwave signal is generated in response thereto which is related to an intensity of the brain wave during the event. Heart beats of the user's heart are detected while the user experiences the event and a heart rate signal is generated which is related to the heart rate of the user during the event. The brainwave signal and the heart rate signal are used to produce an emotional response signal that is related to an emotional response of the user to the event.

Another disclosure involves objectively determining a response of a user to an event in media where amounts of electrical energy in certain bandwidths in the brain of the user are detected. The response of the user is determined based at least partially on the detected amounts of electrical energy.

Yet another disclosure involves objectively determining a response of a user to an event in media where a physical orientation of the head of the user is detected while the user experiences the event. A reaction of the user to the event is determined based on the detected orientation and/or movement of the user's head.

Still another disclosure involves objectively determining a response of a user to an event in media where a level of oxygen in the blood of the user is detected. A reaction of the user to the event is determined based on the detected level of oxygen.

In addition to the exemplary aspects and embodiments described above, further aspects and embodiments will become apparent by reference to the drawings and by study of the following descriptions.

BRIEF DESCRIPTION OF THE DRAWINGS

Exemplary embodiments are illustrated in referenced figures of the drawings. It is intended that the embodiments and figures disclosed herein are to be illustrative rather than limiting.

DETAILED DESCRIPTION

Various modifications to the described embodiments will be readily apparent to those skilled in the art and the generic principles taught herein may be applied to other embodiments. Thus the present invention is not intended to be limited to the embodiment shown but is to be accorded the widest scope consistent with the principles and features described herein including alternatives, modifications and equivalents, as defined within the scope of the appended claims. It is noted that the drawings are not to scale and are diagrammatic in nature in a way that is thought to best illustrate features of interest.

Figure 1:
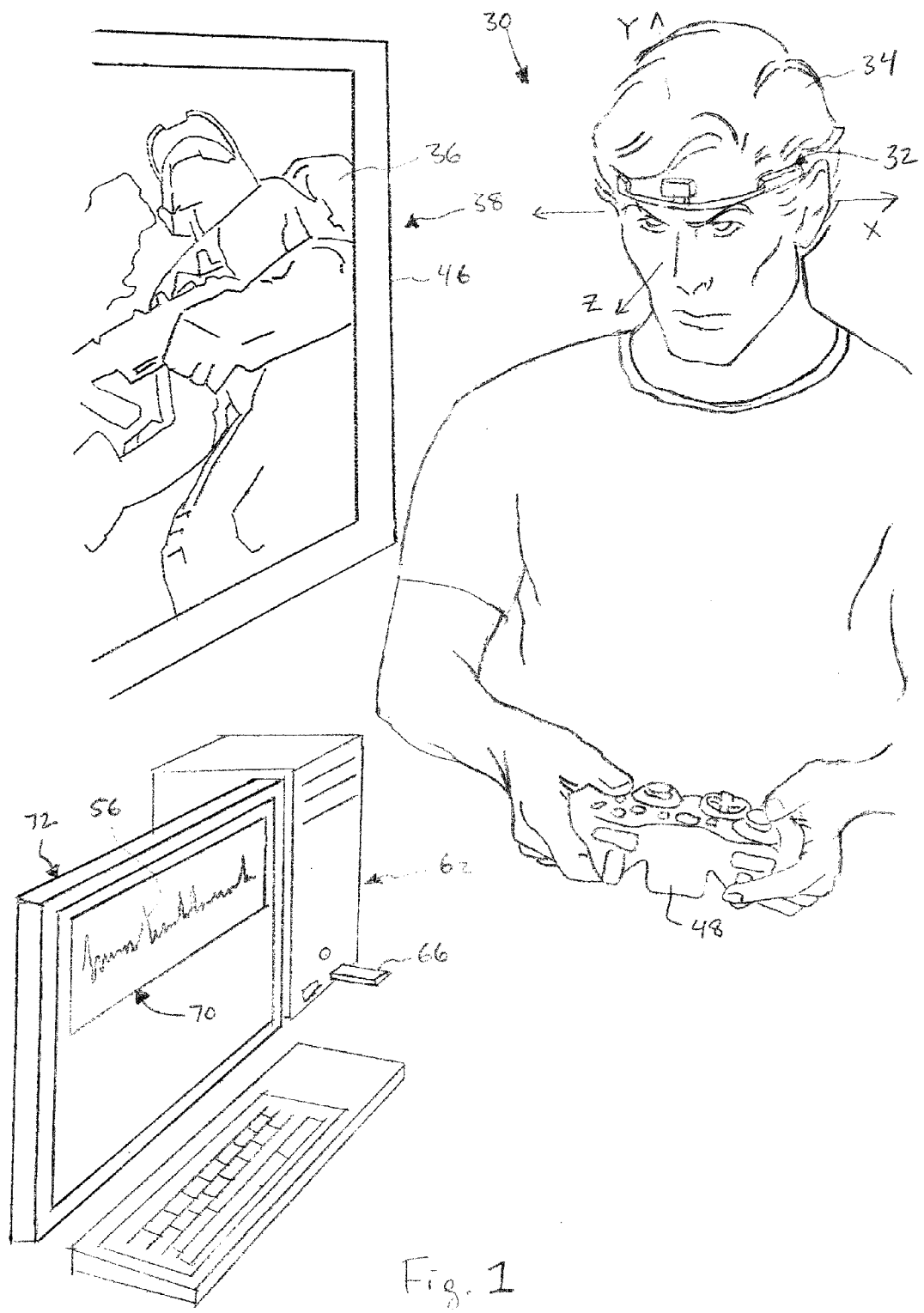
FIG. 1 is a perspective view of a media analysis device connected to a user for analysis of an event in media.
Figure 2:
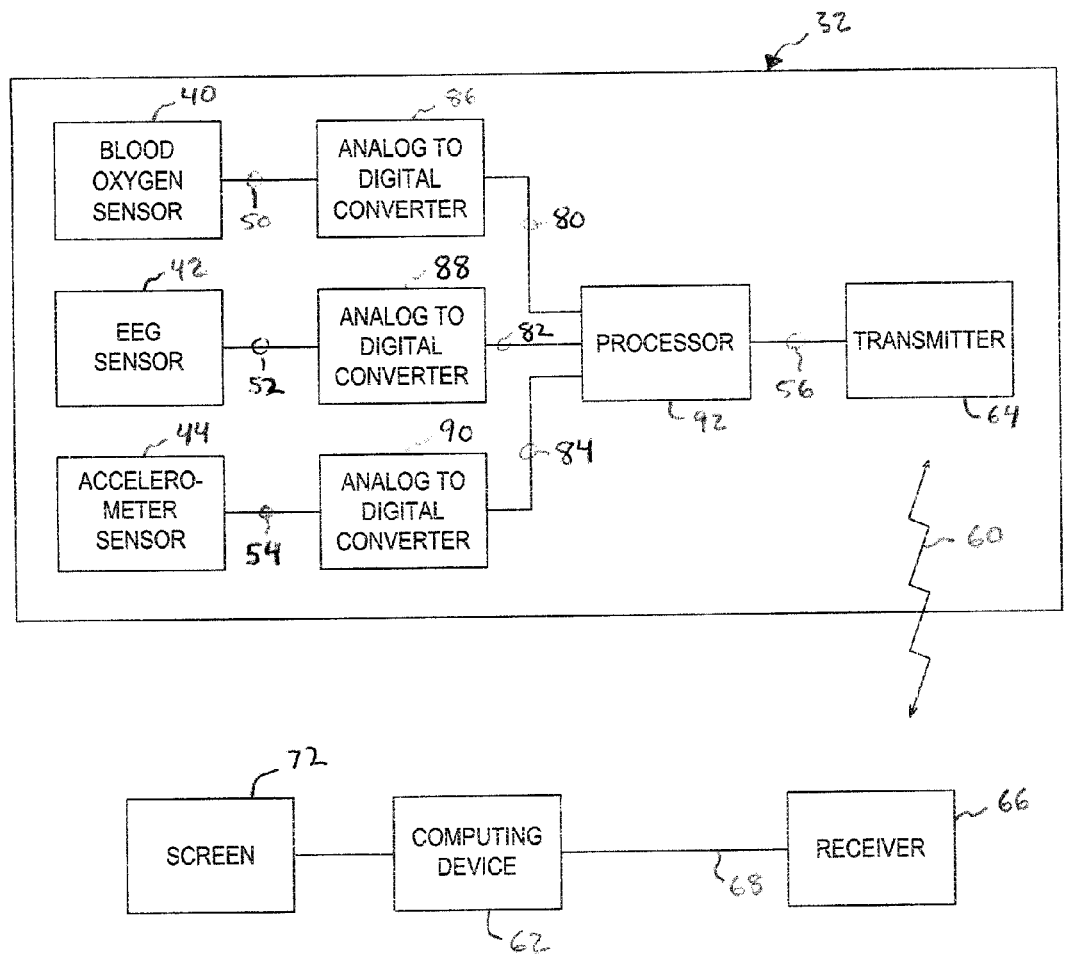
FIG. 2 is a block diagram of the media analysis device shown in FIG. 1 showing physical sensors.

A media analysis device 30 as described in one example herein is shown in FIG. 1. Media analysis device 30 includes a data sensing structure for collecting physiological data, such as head set 32 that is worn on the head of a user 34. Device 30 is used for objectively determining a mental reaction of the user to an event 36 in media 38 experienced by the user. The mental reaction is determined based on physiological changes in the user that are detected with physiological sensors, such as blood oxygen sensor 40, Electroencephalogram (EEG) sensor 42 and accelerometer sensor 44 (FIG. 2). The mobile nature of the head set 32 allows the user to experience the media without restricted movement which allows for the acquisition of information about the mental reaction of the user in a real experience environment.

Media 38 may be visual and/or audible such as a television program, a movie, a video game or other type of sensory input experienced by the user. Media 38, shown in FIG. 1, is a video game that is displayed on a television 46 and is exemplary of the types of media with which device 30 and associated methods are used. The game receives input from user 34 through a controller 48 which interacts with a game console (not shown). Event 36, as shown in FIG. 1, is a segment of a video game during which media 38 is designed to evoke a mental reaction or response in user 34.

Physiological sensors 40, 42 and 44 (FIG. 2) measure the physiological conditions or responses of the user to event 36 and generate blood oxygen sensor signal 50, EEG sensor signal 52, and accelerometer sensor signal 54, respectively, which are related to the responses of the user. Sensor signals 50, 52 and 54 are used to produce a mental reaction signal or data 56 that is related to the mental state or response of the user to one or more events in media. Other types of physiological sensors may also be used, such as skin temperature sensors, skin resistivity sensors and others depending on the mental reaction or reactions that are to be determined.

Sensor signals 50, 52 and 54 are converted into digital sensor signals 80, 82 and 84 using analog to digital converters 86, 88 and 90, respectively (FIG. 2). Analog filtering or other analog processing of sensor signals 50, 52 and 54 may be accomplished prior to converting these signals into digital form.

As will be further described, in the present example, a processor 92 (FIG. 2) receives the digital sensor signals and uses algorithms or methods referred to as derived sensors 100, 102, 104, 106, 108 and 110 (FIGS. 3-8) and virtual sensor 112 (FIG. 9) to create mental reaction data 56 from the data obtained from the physiological sensors.

As seen in FIG. 2, mental reaction data 56 can be transmitted over a wireless link 60 from head set 32 to a computing device 62 or other type of device where the mental reaction data 56 can be displayed and/or stored or processed. Wireless link 60 includes a transmitter 64 in the head set and a receiver 66 connected to the computing device. Receiver 66 can be connected to computing device 62 through a port 68, such as a wireless Ethernet port or USB port. Transceivers can also be used in place of transmitter 64 and receiver 66.

In the present example, mental reaction data 56 is used to produce a graph 70 on a screen 72 of computing device 62 (FIG. 1). Graph 70 represents responses of the user to media 38 over a period of time which includes multiple events. Graph 70 graphically displays mental reaction data 56 in the present example. Graph 70 can be automatically or manually correlated with the events shown in media 38 to determine the user's response to the events. Correlation can be accomplished by determining times at which the events occur in the media and determining values of the mental reaction data 56 at the times corresponding to the events. In this way, an objective determination can be made about the response of the user to any given one of a multitude of events in the media. An objective determination means that the user is not involved in mentally interpreting or verbally communicating the response. The user response is correlated to actual physiological measurements. Mental reaction data 56 can be saved in memory in computing device 62 for later use in analysis of media 38 or for other purposes.

Blood oxygen sensor 40 produces sensor signal 50 based on an amount of oxygen in the blood of the user at any given time. In the present example, the sensor is mounted to the head set and is positioned next to the forehead of the user. In this position, the blood oxygen sensor 40 detects the amount of oxygen in blood vessels in the user's forehead. When the user breathes, the level of oxygen in the blood increases and, when the user's heart beats, the number of red blood cells carrying the oxygen in the forehead increases.

EEG sensor 42 produces sensor signal 52 based on energies of brain waves in certain bandwidths. Delta band brain waves are less than about 4 Hz; Theta band brain waves are about 4-8 Hz; Alpha band brian waves are about 8-12 Hz; and Beta band brain waves are about 13-30 Hz. In one example of an EEG sensor, one electrode of the EEG sensor is positioned in the head set to contact the forehead of the user at a position where the electrical activity in the brain is to be sensed or measured. Another electrode of the EEG sensor is a reference electrode and is positioned a small distance away from the point where the sensor electrode is placed. An EEG sensor that can be used for the present purposes is disclosed in co-pending application Ser. No. 11/500,678 which is incorporated herein by this reference. Other types of EEG sensors can also be used.

Accelerometer sensor 44 produces sensor signal 54 based on movement and/or orientation of the user's head. Data gathered from the accelerometer sensor 44 can be related to acceleration of the head in three dimensions as well as orientation of the head of the user. Accelerometer sensor 44 can produce three signals, one for each of the X, Y and Z dimensions or directions of movement. The three signals can be combined, using Equation 1 below, to give the energy over all three dimensions. While each of the dimension signals can be used separately, they can be combined for determining noise and determining overall power with a Fast Fourier Transform (FFT) as discussed below. Any suitable technique can be used for identifying the signal frequency components of signals that are processed throughout this disclosure. The use of the FFT is exemplary.

$$\text{Combined signal from sensor } 44 = \sqrt{x^2+y^2+z^2} \quad \text{Equation 1:}$$

The mental reaction data 56 is exemplary of the types of data which can be produced by media analysis device 30. In the present example, mental reaction signal 56 is related to how mentally engaged the user is in the event. Mental engagement can be determined using derived sensors 100, 102, 104, 106, 108 and 110 (FIGS. 3-8). Derived sensors are algorithms or methods that operate on processor 92 that each take one or more physiological sensor signals 50, 52 and/or 54 and create derived sensor signals that correspond to specific features or characteristics of the physiological sensor signals used in the derived sensors.

Signals from physiological sensors and/or derived sensors can be combined or used in virtual sensor functions or methods along with context information to create a measure of the user's response. Context information plays two roles: it provides the virtual sensor with information about how to calculate an output from the given inputs and also provides information about how the output of the virtual sensor should be interpreted.

In some instances, a virtual sensor can be modeled as a polynomial with coefficients k0, k1, k2, etc., as shown in Equation 2.

$$\text{Virtual Sensor } X = k0 * f(\text{blood oxygen signal}) + k1 * f(\text{EEG signal}) + k2 * f(\text{heart rate signal}) + \ldots \quad \text{Equation 2:}$$

The coefficients k0, k1, k2, etc. tell Virtual Sensor X how much weight it should give to all of its component sensors. For example, if Virtual Sensor X only uses data from blood oxygen sensor 40, then k0 is equal to 1 and all of the other coefficients are equal to zero in Equation 2.

Context data is also used for interpreting the output of the virtual sensor, depending on the context of the inputs. For example, when the user is placed in an exciting situation in anticipation of experiencing happiness, the user's response is very similar to that of someone placed in a fearful situation. Therefore, only when the user's situation is understood can the meaning of the virtual sensor output be derived.

The virtual sensor also allows for the measurement of confidence in its own output and the outputs from the individual component sensors, (either physiological or derived). For each of the component sensors, a virtual sensor can access a metric which indicates a level of confidence in the data from the component sensor. For example, if a heart rate derived sensor is producing an output that indicates that the user's heart rate is 300 beats per minute, the heart rate is compared with a metric of a range of possible heart rates and a determination is made that the data is most likely erroneous. The weight given to that component sensor is then reduced. One form of a virtual sensor which includes a confidence aspect is shown in Equation 3 below.

$$\text{Virtual Sensor } X = k0 * f(\text{blood oxygen signal}) * \text{confidence}(\text{blood oxygen signal}) + k1 \ldots \quad \text{Equation 3:}$$

The virtual sensor can also measure the confidence in the output of the virtual sensor. If, for example, Virtual Sensor X is made up of three component sensors, and all three provide indicators that the output of Virtual Sensor X should increase, then Virtual Sensor X will have a high confidence that it should produce a higher output. However, if only two of the component sensors indicate that Virtual Sensor X should increase, and the other component sensor provides a strong indication that the Virtual Sensor X should decrease, then Virtual Sensor X may still increase its output, however there will be a much lower confidence in the output. An example of such a virtual sensor is shown in Equation 4.

$$\text{Virtual Sensor } X = \text{coherence\_confidence\_function} * (k0*(\text{blood oxygen signal})*\text{confidence}(\text{blood oxygen signal}) + k1 * \ldots \quad \text{Equation 4:}$$

Figure 9:
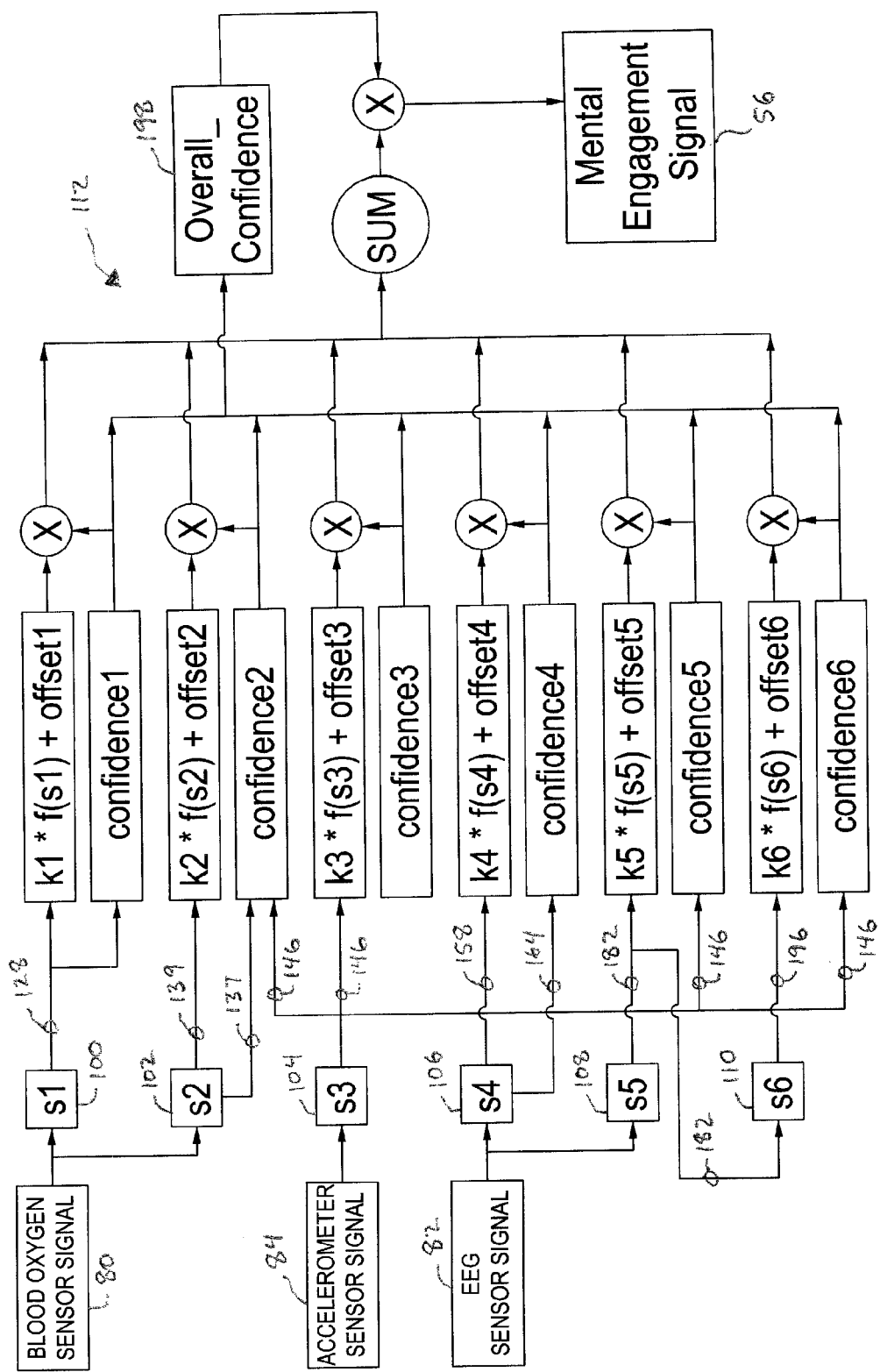
FIG. 9 is a block diagram of a virtual sensor using the derived sensors shown in FIGS. 3-8 used in analysis of the event.

Referring to FIG. 9 in conjunction with equation 5, a virtual sensor is shown in block diagram and equation form, respectively. In the present example, derived sensors 100, 102, 104, 106, 108 and 110 are used in a virtual sensor algorithm 112 to create mental reaction data 56 representing the emotional response of the user to the event. The derived sensors in this example use data from physiological sensors 40, 42 and 44.

$$\text{Mental Engagement} = \text{Overall\_Confidence} * (((k1*f1(s1)+\text{offset1})*\text{confidence1}) + ((k2*f2(s2)+\text{offset2})*\text{confidence2}) + ((k3*f3(s3)+\text{offset3})*\text{confidence3}) + ((k4*f4(s4)+\text{offset4})*\text{confidence4}) + ((k5*f5(s5)+\text{offset5})*\text{confidence5}) + ((k6*f6(s6)+\text{offset6})*\text{confidence6})) \quad \text{Equation 5:}$$

The functions f1, f2, f3, f4, f5 and f6 take signals from derived sensors 100, 102, 104, 106, 108 and 110 (s1, s2, s3, s4, s5 and s6 in Equation 5) as inputs and, in turn, output values for determining mental reaction data 56, related to the mental engagement of the user. Sensors 100, 102, 104, 106, 108 and 110 generate sensor signals 128, 137, 139, 146, 158, 164, 182 and 196 shown in FIGS. 3-9. Signals resulting from the virtual sensor, functions, derived sensors and the physical sensors can all be considered to be physiological response signals since they are based on the physiological response of the user.

Function f1 takes s1 as an input and calculates the derivative of s1, and returns the value of (s1+the derivative of s1). Function f2 takes s2 as an input and returns s2 as the result, in which instance derived sensor s2 is useful by itself. Function f3 takes the value of s3 and finds the amount of energy between 1-3 Hz and returns a negative of that value. Function f4 takes s4 as an input and returns s4 as the result. Function f5 takes s5 as an input and returns s5 as the result. Function f6 takes s6 as an input and returns a result that is equal to 60-s6.

In the equation, k1, k2, k3, k4, k5 and k6 are context values which determine an amount of weight that is given to each function f1, f2, f3, f4, f5 and f6 respectively. In the present example, k1=0.7; k2=0.06; k3=0.06; k4=0.06; k5=0.06 and k6=0.06. These context values can be defined by correlating the output of each vector with data from an application, such as survey data or other reported metrics. An amount of each component is then determined based on this data. The offsets (offset1 to offset6 are used to shift the value of the functions up or down and in the present example all of the offsets, (offset1 to offset6) are set to zero. In one instance, the offsets can be used for normalizing aspects of the signal across multiple users, such as instances where the virtual sensor or function has an average value that is non-zero. In some circumstances, where the virtual sensor trains itself on multiple user's, the offsets can be used to change the output value based on the training.

The values of confidence1 through confidence6 are each a scaling factor having a value from 0 to 1 that is related to how much confidence there is in the value of the corresponding derived sensor signals. Each of the values of confidence is either related to one or more of the derived sensor signals, or may be set to a constant.

Figure 3:
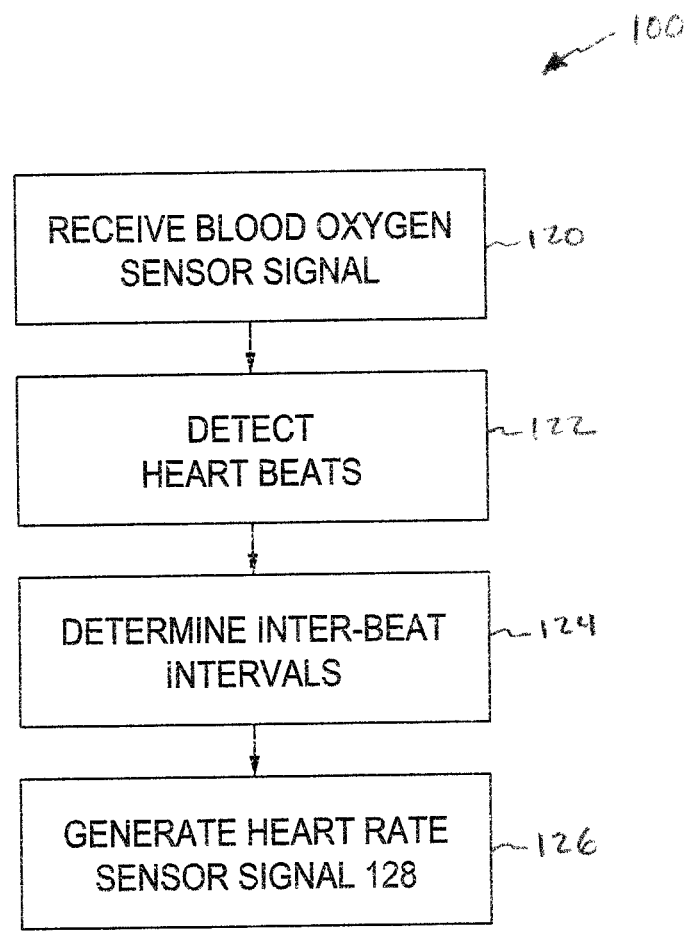
FIG. 3 is a flow chart of a derived sensor determined from a physical sensor shown in FIG. 2.

Derived sensor 100, which is related to heart rate, is shown in FIG. 3. Derived sensor 100 begins at step 120 where digital blood oxygen sensor signal 80 is received by processor 92. Following step 120, the sensor proceeds to step 122 where the heart beats in the blood oxygen signal 80 are detected. Heart beats are detected, in the present example, by determining peaks in the blood oxygen which correspond to increases in oxygen carrying blood cells caused by pumping of the heart. The blood oxygen sensor signal 80 is sinusoidal and the processor detects the peaks of the signal using a peak detector. Following the determination of the heart beats, derived sensor 100 proceeds to step 124 where an inter-beat interval between the heart beats is determined. The inter-beat interval is inversely related to the heart rate of the user. Derived sensor 100 then proceeds to step 126 where a heart rate derived sensor signal 128 (FIG. 9) is generated.

Figure 4:
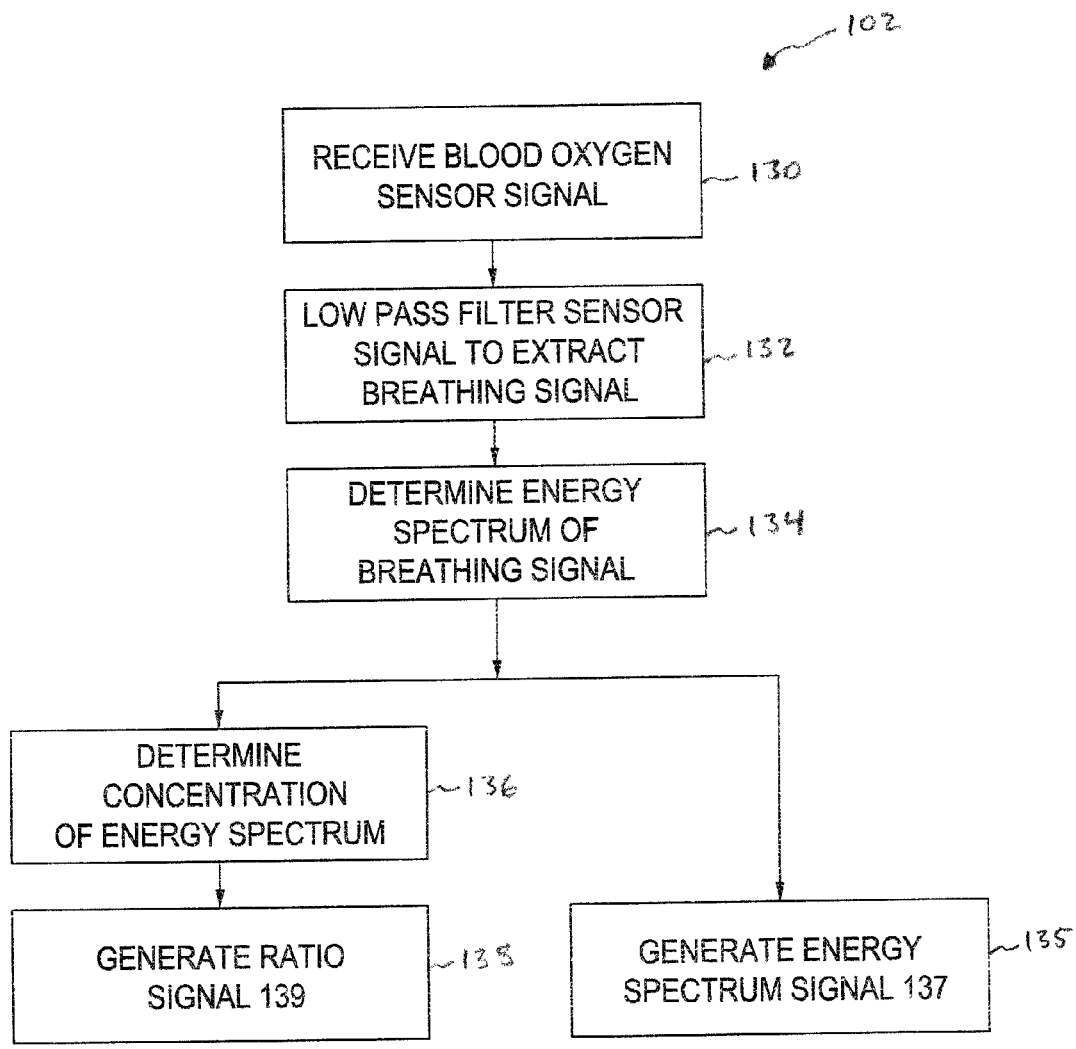
FIG. 4 is another flow chart of a derived sensor determined from a physical sensor shown in FIG. 2.

Derived sensor 102, shown in FIG. 4, also uses the digital blood oxygen sensor signal 80. Derived sensor 102 is related to the coherence of the breathing of the user and begins at step 130 by receiving digital blood oxygen sensor signal 80. The sensor 102 proceeds from step 130 to step 132 where sensor signal 80 is low pass filtered to extract a breathing related component of the sensor signal. Although the blood oxygen sensor signal 50 is sinusoidal, the overall amount of oxygen in the blood is determined by breathing. This changes the offset of sensor signal 50 and represents a low frequency component of the signal. By low passing sensor signal 50, the frequency component related to heart beat is removed and the remaining lower frequency component is related to breathing.

Following the low pass filtering in step 132, the derived sensor proceeds to step 134 where the power spectrum of the breathing related signal is determined. Step 134 uses a FFT to determine the energy concentration before the derived sensor 102 proceeds to step 136. In step 136, the concentration of the energy spectrum above and below about 0.2 Hz is determined from the information found by the FFT. If most of the energy in the spectrum is concentrated in frequencies below about 0.2 Hz, then the breathing is considered to be coherent. If, on the other hand, the breathing involves choppy, quick breaths, the breathing is considered incoherent and most of the energy in the spectrum will be concentrated in the frequencies above about 0.2 Hz.

Following the determination of the concentration of the energy spectrum in step 136, the derived sensor 102 proceeds to step 138 where a breathing coherence signal 139 (FIG. 9) is produced. The breathing coherence signal is a ratio of the energy in the frequencies less than about 0.2 Hz to the energy in the frequencies greater than about 0.2 Hz. Derived sensor 102 also branches from step 134 to step 135 where an energy spectrum signal 137 is generated, as will be further described.

Figure 5:
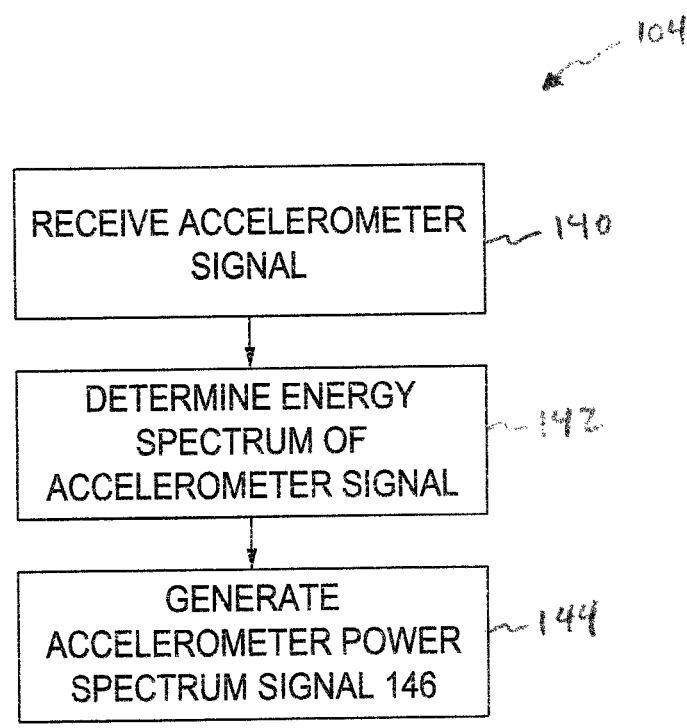
FIG. 5 is another flow chart of a derived sensor determined from a physical sensor shown in FIG. 2.

Derived sensor 104, shown in FIG. 5, receives the accelerometer sensor signal 54 at step 140. Derived sensor 104 then proceeds to step 142 where a FFT is performed on signal 54 to determine the energy spectrum of the accelerometer sensor signal. Following step 142 sensor 104 proceeds to step 144 where an accelerometer power spectrum signal 146 (FIG. 9) is produced.

Figure 6:
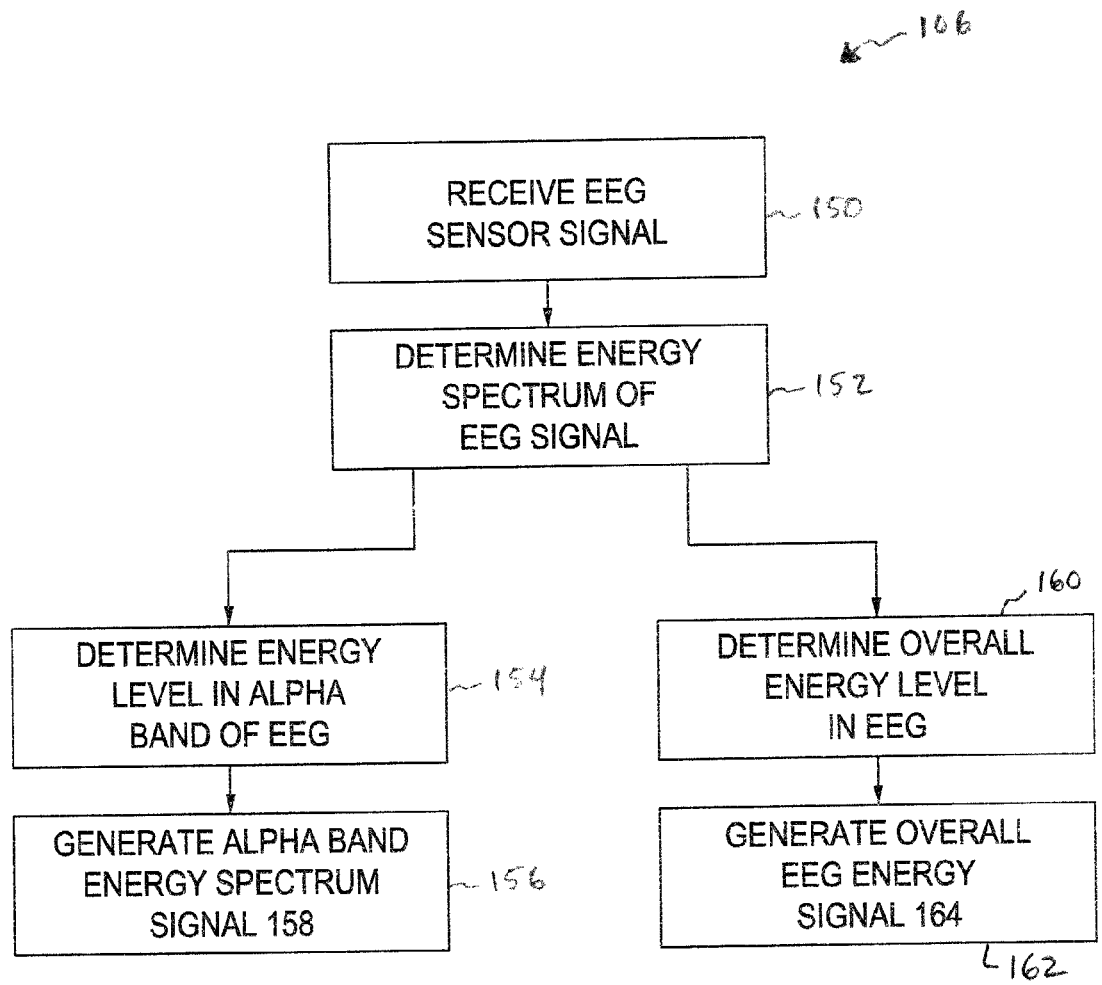
FIG. 6 is another flow chart of a derived sensor determined from a physical sensor shown in FIG. 2.

Derived sensor 106 is shown in FIG. 6. Derived sensor 106 begins at step 150 where sensor 106 receives EEG sensor signal 52. Following step 150, an FFT is taken of the EEG sensor signal at step 152. After step 152, derived sensor 106 follows two branches of action. In one branch of action, sensor 106 proceeds to step 154 where an energy level in an Alpha band of the EEG is determined. Following step 154, the derived sensor 106 proceeds to step 156 where an Alpha band energy signal 158 (FIG. 9) is created. In the other branch of action, sensor 106 proceeds to step 160 where an overall energy of the EEG is determined using the data from the FFT taken in step 152. After step 160, the derived sensor 106 proceeds to step 162 where an overall EEG energy signal 164 (FIG. 9) is generated.

Figure 7:
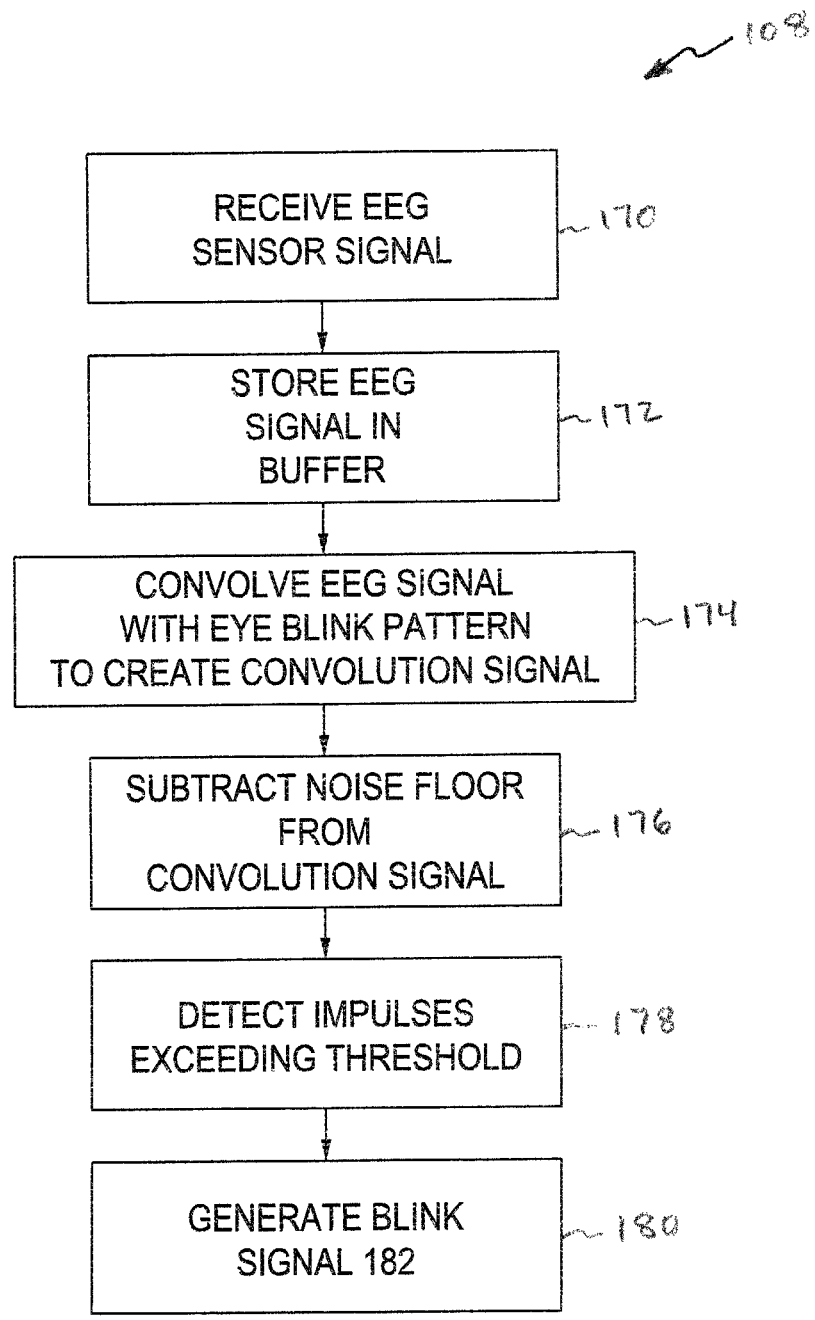
FIG. 7 is another flow chart of a derived sensor determined from a physical sensor shown in FIG. 2.

Derived sensor 108, shown in FIG. 7, is used in determining if the user has blinked and begins at step 170 by receiving the EEG sensor signal 52 from the EEG sensor. EEG sensor signal 52 is then stored in a buffer in step 172. After the EEG sensor signal is buffered, derived sensor 108 proceeds to step 174 where the buffered EEG sensor signal is convolved with an eye blink pattern to produce a convolution signal. The eye blink pattern is an average response to recorded data of multiple viewers blinking. Following step 174, the derived sensor proceeds to step 176 where a noise floor is subtracted from the convolution signal. The noise floor is data that is previously calculated from data where viewers are not blinking. Once the noise floor is subtracted at step 176, derived sensor 108 proceeds to step 178 where the signal resulting from step 176 is examined for impulses with amplitude that exceeds a predetermined threshold level. A blink of the user's eye is determined to have occurred when the amplitude exceeds the threshold limit. Following step 178 is step 180 where a blink signal 182 (FIG. 9) is produced.

Figure 8:
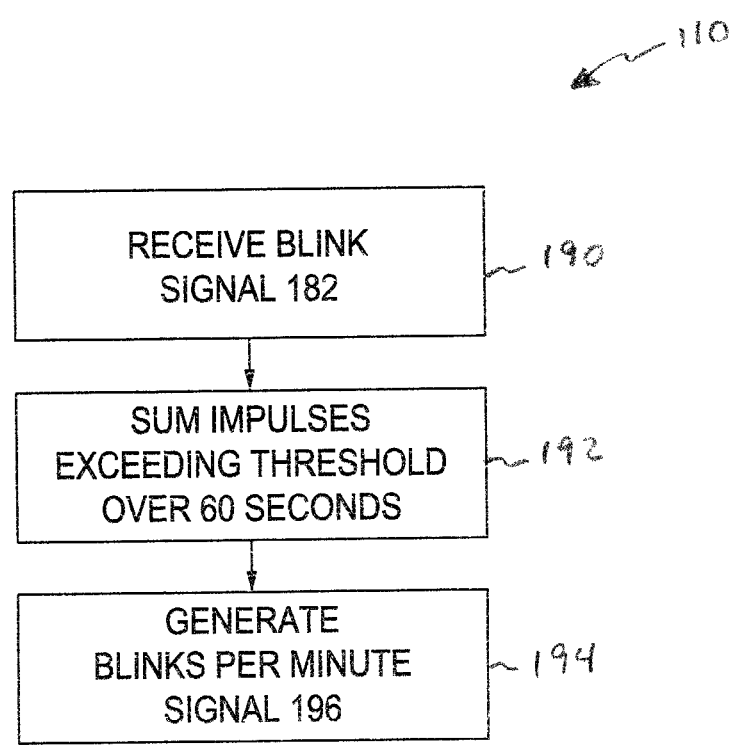
FIG. 8 is another flow chart of a derived sensor determined from a physical sensor shown in FIG. 2.

The last derived sensor used in the present example is derived sensor 110, shown in FIG. 8. Derived sensor 110 begins at step 190 where blink signal 182 is received. Following step 190 is step 192 in which the number of impulses that exceed the threshold limit are added over a period of 60 seconds. Following step 192 is step 194 in which a blinks per minute signal 196 (FIG. 9) is produced.

A unique aspect of the present device is that the scaling factors of the confidence values are not necessarily based on the function or derived sensor that they are used to scale. Some of the scaling factors used to scale one function of a derived sensor are based on a different derived sensor. Some functions or derived sensors which utilize inputs from one type of physical sensor are scaled using information from an entirely different physical sensor. An example of this situation is illustrated by the block diagram in FIG. 9.

In the present example, confidence1 is based on derived sensor signal 128 (s1). If derived sensor signal 128 were to change more quickly that humanly possible, or if it has a value that is too low or too high, then the scaling factor is reduced. For example, if derived sensor 100 were outputting values such as 300 beats per minute, then the scaling factor of confidence1 is reduced.

Confidence2 uses the value of derived sensor signal 146 from derived sensor 104 (s3) and the power spectrum signal 137 from derived sensor 102 (s2). If the value of derived sensor signal 146 is similar to power spectrum signal 137, then confidence2 is reduced proportionally with the correlation between the two power spectrums. This is because noise is created when a user's head moves. This noise is seen on both the EEG and accelerometer signals, showing up as "blips" or spikes in the signals. More correlation between the two power spectrums, (when motion in non-zero), indicates that more noise is present in the EEG signal so the signal is less accurate.

Confidence3, in the present example is set to a constant value of 1. If the overall amount of energy in the EEG is too high, then confidence4 is reduced proportionally. The overall amount of energy may be too high due to noise in the system.

Confidence5 is one example where data from one physical sensor is used in scaling a function based on another physical sensor. In this case, if the overall amount of energy in derived sensor signal 146 (based on the accelerometer) is too high, then confidence5 is reduced proportionally. Confidence5 is used for scaling f5 which is a function based on EEG.

Confidence6 uses derived sensor signal 146 in determining the scaling factor of f6. When the overall energy of derived sensor signal 146 is too high, then confidence6 is reduced proportionally.

Overall_Confidence 198 is a scaling factor for the entire virtual sensor. This value is determined by the number of components that register an increase in value. For example, if confidence1, confidence2 and confidence 4 to confidence6 all go up, then the Overall_Confidence 198 will be high. However, if confidence1 and confidence2 go up while confidence4, confidence5 and confidence6 go down, then Overall_Confidence 198 will be low.

The scaling factors of confidence1, confidence2, confidence3, confidence4 and confidence6 can be changed while the physiological response of the user is being detected, in the present example. In other examples, the scaling factor can be changed in part or wholly as a response to a rate of change of one or more of the physiological response signals or based on other characteristics of physiological responses.

Other types of characteristics of the physiological responses can be used for adjusting the scaling factor of one or more sensor or mental reaction signals. Another of these characteristics which can be used for adjusting the scaling factor relates to a rate of change of a physiological response or condition of the user. One example of this is when the rate of change exceeds what is physiologically possible. In these instances, the scaling factor is decreased if the rate of change of a selected response signal is greater than a predetermined rate of change.

The above exemplary virtual sensor uses three types of physiological sensors and six different derived sensors. Other virtual sensors may use more or less physiological sensors and derived sensors as well as different types of these sensors. Many times, the physical response as detected by one or more of the physical sensors does not directly correlate to an emotional response or mental reaction without further manipulation. The virtual sensors and derived sensors take the raw data from the physical sensors and process the raw data into signals that more closely represent the emotional response of the user. A derived sensor is an algorithm that uses input from physiological sensors to create signals related to the physiology but not necessarily directly related to the physiology. Some types of mental reaction signals are based on a single derived sensor signal alone, without the additional processing or manipulation of a virtual sensor.

Some additional types of physiological sensors include skin resistance and skin temperature sensors, for instance. Skin resistance is used as an indicator of response for measuring the same phenomena that makes the palms of your hands sweaty when you are nervous. Skin resistance is an involuntary response that you can not control. It is the primary sensor in a lie detector. When you hear something or see something and you have a clinch or nervous response there is a rapid change (drop) in skin resistance a few milliseconds later. This response only lasts a short time (less than a second). The measure is not very robust in that it requires very good continuous contact with the skin. This means that the person can't move. It also tends to be something that "requires an expert" to decode. This is because the response varies from person to person and you need to look at it relative to other responses. Skin resistance is used in biofeedback to identify things that a person has a strong response to and to "train" them to have a lower response.

Skin temperature is a measure of arousal. When something provokes a fear, anger, or love response, the body shifts the blood flow to or from the skin and you get an increase or decrease in skin temperature. Measurements of skin temperature and skin resistance can be used to determine an emotional response of a user to an event either separately or in conjunction with other measurements.

Other types of derived sensors are also based on signals from blood oxygen sensor 40, EEG sensor 42 and/or accelerometer sensor 44.

One EEG based sensor determines amounts of Theta band EEG energy in the frontal areas of the user. Increased Theta band EEG energy indicates increases in the stressfulness or mentally engaging aspects of the media.

Another EEG based sensor determines overall brain activity by taking an FFT of the EEG data and summing the energy in each frequency to determine the total amount of energy, for example, Delta band+Theta band+Alpha band+Beta band. Another sensor determines which frequencies contain the most energy by taking an FFT of the EEG data, and still another sensor is calculated by taking an FFT of the EEG data and summing the energy in the individual frequencies to determine the amount of energy in the Alpha band. Higher Alpha band energies, relative to a base line, correspond to less thought and a feeling of relaxation.

A mental engagement sensor takes data from the EEG related to the energies in the Theta and Alpha bands and calculates a ratio of the energies. In one example, the ratio of energies are calculated using (Theta−Alpha)/(Theta+Alpha). Another example calculates the ratio of energies using Theta/Alpha. The result of the ratio calculation is low pass filtered with a filter set at 1 Hz, in one example. Increases in energy in the Theta frequency band correlates to an increase in thought processing. Decreases in energy in the Alpha band correlates with a decrease in thought processing. The result of the mental engagement sensor provides an objective measure of mental processing. A surprise related sensor is determined by taking the positive deriative of the signal from the mental engagement sensor.

Beta band EEG frequencies (about 13-30 Hz) have very short event widths and therefore correspond to mental activity that operates very quickly. Decreased beta energy can be indicative of depression. Increased beta energy correlates with periods of recognition and engagement.

A relaxation related sensor is calculated by applying a scale factor to the amount of energy in the EEG Alpha band. The result is then low pass filtered at a frequency of 1 Hz, in the present example. The result of the calculation is indicative of the level of relaxation of the user during the event in the media.

A happiness related sensor is used for determining if the user is happy during the event. This sensor is based on differences in data coming from a left EEG sensor and a right EEG sensor. A difference is found between Alpha energy from the left EEG sensor and Alpha energy from the right EEG sensor. In one example, these energies are used in the following formula: (Left Alpha Energy−Right Alpha Energy)/Left Alpha Energy+Right Alpha Energy). Another exemplary formula is: Left Alpha Energy−Right Alpha Energy. The result of the calculation is low pass filtered, in one instance at 0.6 Hz, to reduce the high frequency noise. The resulting signal includes characteristics which are indicative of how happy the user is. The higher the signal level from the happiness related sensor, the more positive the response to the event that was experienced.

An attention related sensor is calculated using EEG data that has been processed using the blink detector derived sensor 108 or another algorithm for determining blinks. An average number of blinks is calculated over a one minute interval. The inverse of the average number of blinks is determined, in one instance, by taking 1−(average number of blinks), in another instance, by taking 1/(average number of blinks). The result of the inverse is low pass filtered, for example at 1 Hz. The resulting data is characteristic of the degree of the user's attention.

An accelerometer based sensor measures the orientation of the head of the user using a three axis accelerometer mounted on the user's head. In this example, the accelerometer outputs a value for each of three axes of the accelerometer, shown in FIG. 1 as X, Y and Z. The three axes correspond to the axes of rotation in the head motions of nodding (up and down), rotating (left and right), and tilting (left and right), respectively axes X, Y and Z. For each axis of motion of the accelerometer, the value outputted by the sensor is either a positive or negative amplitude. If the head is still, then that output values are determined by how the axes are aligned with respect to gravity, which always produces a constant acceleration in the direction of the floor. Given this information, it is possible to find the head's orientation. For example, when the user's head is held in the down position, where the eyes are facing towards the floor, the value for the "nod" X axis will be negative (with the amplitude determined by how close the user's head is to vertical) and the values for the other two axes will remain at zero. This is because in this circumstance there is rotation around the X axis shown in FIG. 1. The triplet of values, negative-zero-zero, becomes the "head down" case. Using this technique, all of the possible orientations of the user's head can be mapped. In one instance, the user's head orientation can be used to determine if the user's head has been cocked in thought.

Another accelerometer based sensor is used to determine if the user is speaking. This sensor is calculated by taking the combined data from accelerometer sensor 44 and performing a band-pass filter on the data between approximately 150 and 300 Hz. A FFT is then taken of the filtered signal and the total energy in the band is then calculated. Higher levels of energy in the band are indicative that the user is speaking. Other information about mental reaction can also be determined by movement of the user's head. Vibration or shaking can be correlated to the user's stress level. Nodding the head up and down or back and forth can indicate positive and negative responses, respectively.

A patience related sensor also uses data from the accelerometer. In this instance, an average amount of movement of the user is determined over a one minute time window. An inverse of the average amount of movement is determined and a scaling factor is then applied. The resulting signal is related to how patient the user is during the event or events in the one minute time window. The more jittery the user is, the less relaxed and patient the user is. The patient related sensor can be normalized for each user to create a session long patient value.

Another type of blood oxygen sensor based sensor determines a characteristic of the heart pulse. The value of this derived sensor is calculated by finding the integral of the second half of the sinusoidal signal from the blood-oxygen physiological sensor. First, the maximum and minimum of the blood-oxygen signal are found. Then a point in time T is found when the signal crosses the 50% mark between its max and min. The area between the signal and the signal's minimum value is then found by integrating from time T to the time when the signal returns to its minimum value. This derived sensor is used to determine levels of stress.

An adrenaline related sensor also uses data from the blood oxygen sensor. The adrenaline sensor is used for determining a mental reaction of the user to the event based on adrenaline type response to the event. In this sensor, the heart rate data is taken and the data is normalized by removing the user's average heart rate. A low-pass filter is then taken of the normalized data. The low-pass filter, in one embodiment, is set at 1 Hz to remove higher frequency noise. A scale factor is applied to the filtered signal before the signals is again filtered with a low-pass filter, which can also be set at 1 Hz. The resulting signal is indicative of a mental reaction to the event which causes adrenaline to be released in the user.

Another example of an adrenaline related virtual sensor uses a positive derivative of the heart rate of the user with a 5-second smooth applied to the signal. The use of the five second smooth eliminates any heart rate variance data and only includes unanticipated rises in heart rate caused by excitement or adrenaline release. Slew rate and low pass filtering can both be used for smoothing.

Data from the blood oxygen sensor is also used in a fright related sensor. The fright related sensor is used for determining if the user is frightened by an event. The average of the user's heart rate is determined over a 10 second window, in one example. If the average value is higher than the user's overall average heart rate, then the user may be considered to be in a frightened state. Accelerometer data can also be used to sense if the user jumps in fright or is shaking slightly, which corresponds to fright.

Another example of a sensor which uses information gathered from more than one physiological sensor is an engagement virtual sensor. This sensor involves the determination of the level of engagement of the user during the event in the media, and in the multiple events throughout the media. In media that has a lot of action, engagement in the media correlates to the difference between a measure of the user's heart rate and the amount of thought, e.g. the amount of brain activity in a difference between amounts of energy in the Theta and Alpha bands. If the user's heart rate increases and their thought decreases, the user is highly engaged in the media. If the heart rate stays low and the user thinks more, as indicated by increased brain activity in the Theta and Alpha bands, the engagement of the user in the media is low.

A startle sensor also uses information from more than one physiological sensor. The startle sensor is used for determining if the user is startled during an event. A blink is detected, such as by using the derived sensor 108 shown in FIG. 7, and the user's heart rate is also determined. An increase in the user's heart rate in a time window surrounding the blink is indicative that the user was startled.

In some instances a profile is created for individual users in relation to each media. The profile contains the user's response to the media over a session time, during which the user is exposed to the media. In addition or as an alternative to graphing and displaying the results, statistics are calculated for each profile (for instance, the average value of engagement across the user's session) as well as across profiles (for instance, the average level of engagement of different users during a particular event). Statistics are also used to determine deviation during a specific event, such as a change in engagement over the duration of a particular event, as well as general deviation during the entire session. Statistics used for these purposes include means, standard deviations, derivatives/changes, differences between maximum and minimum, and others. Statistical analysis can be accomplished by calculating an average value point by point across the different users.

As an example, statistics are used to determine to what degree a particular media is coherent, i.e. how much variation is seen in the responses of multiple users. More successful media elicits a more consistent or similar response from multiple users. Less successful media has more scattered responses across the multiple users. Statistics used with the media analysis device 30 allows for the quantification of the differences between media that is successful and unsuccessful.

Statistical and other evaluation techniques also introduce a value concept to the responses, i.e. good responses and bad responses. For example, if the media presents an event designed to be humorous, the profile is the response of the user to the humorous event. If the evaluation determines that the user laughed during the event, then the evaluation is good and if the user did not laugh, then the evaluation is bad.

Computing device 62 can also be used for building a model that correlates user profile characteristics with media success and for comparing the model to user profiles for predicting media success. Pattern matching algorithms or techniques such as neural networks, Bayesian algorithms, support vector machines, nearest neighbor algorithms and machine learning algorithms can be used for evaluating the response of the user to the media by comparing the user's response with responses of other users. With this information, a model can be produced which can be used to predict whether media will produce the desired responses in a user.

Figure 10:
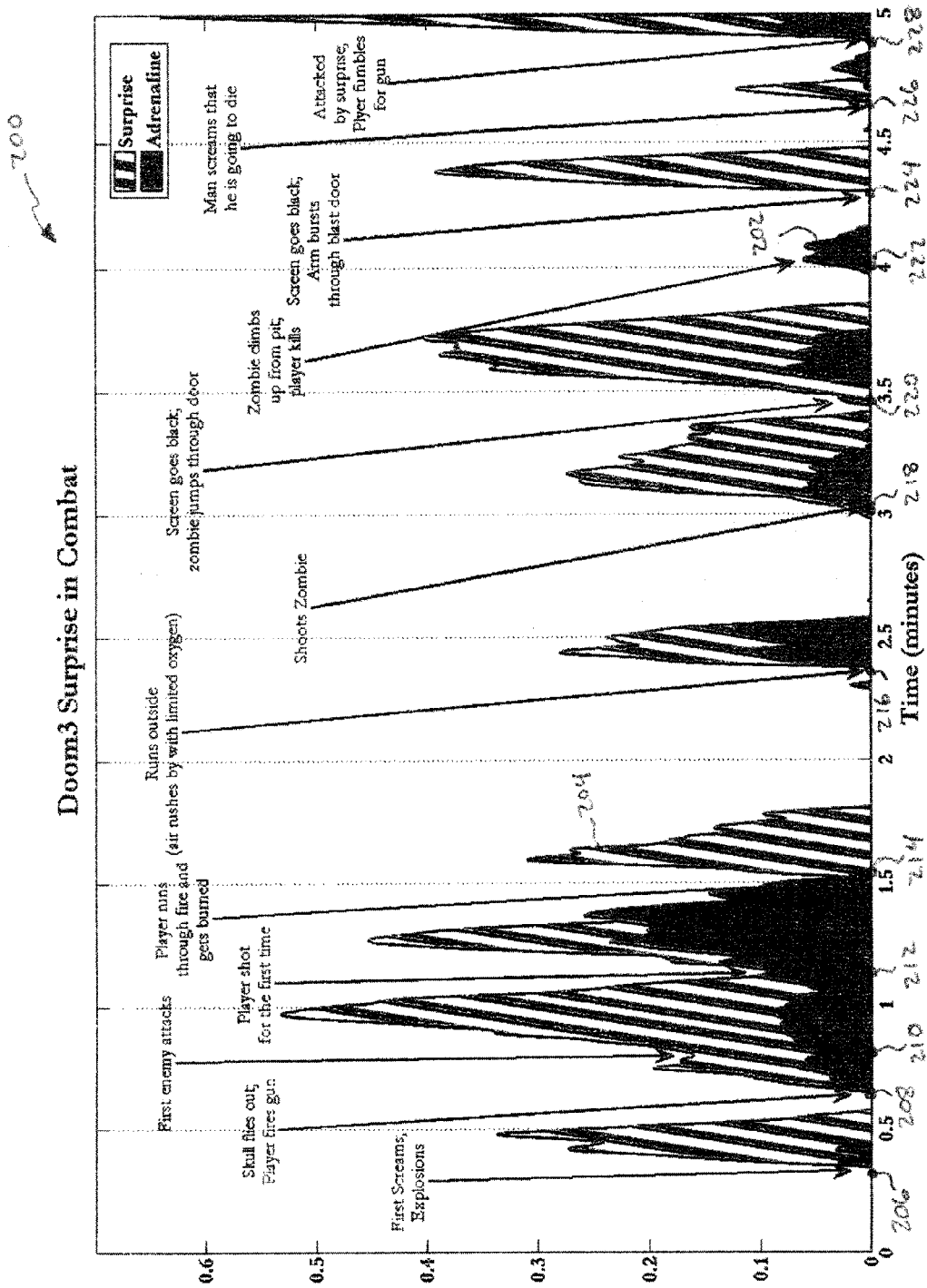
FIG. 10 is a graph of mental and physical reaction signals from the media analysis device shown in FIG. 1.

Exemplary empirical results of the use of an adrenaline sensor and a surprise sensor are shown in a graph 200 in FIG. 10. In this example, the user is playing a game with events that are designed to surprise and excite the user while the user is connected to media analysis device 30. The game in this instance is what is commonly referred to as a first person shooter type game in which the user assumes the identity of character in the game to experience and interact with the game. Graph 200 shows a response signal 202 of mental reaction data from the adrenaline sensor and a response signal 204 of mental reaction data from the surprise sensor. Graph 200 shows amplitudes of response signals 202 and 204 for a 5 minute period during which several events occur.

The events occurring in the game during the time shown in graph 200 are referenced along the time line at the bottom of the graph. At time 206 an event involving screams and explosions occurs in the game. As seen in graph 200, surprise response signal 204 (filled underneath with lined pattern) increases rapidly while adrenaline response signal 202 also increases somewhat. At time 208 a skull flies out and the user fires a gun, both the response signals increase, and before any significant decrease in the response signals, a first enemy attacks at time 210. The enemy attack at time 210 dramatically increases the response signals as seen in graph 200.

At time 212, the user is shot for the first time causing a large increase in adrenaline and surprising the user. Another event occurs at time 214 where the user runs through fire and gets burned. This event causes an increase in the surprise related response signal, but does not increase the adrenaline response signal. Gameplay continues without significant adrenaline or surprise responses until time 216 where the user runs outside and experiences air rushing by with limited oxygen causing an increase both of the response signals. Another break in the action occurs until time 218 when the user shoots a zombie causing an increase in the response signals. After the response signals have returned to a lower level, the screen goes black at time 220 and a zombie jumps through a door causing the user to be surprised and increasing the adrenaline in the user. Following a brief period after the response signals have decreased a zombie climbs up from a pit at time 222 and the user kills it, causing a small increase in the adrenaline response signal but no appreciable surprise response. At time 224, the screen goes black and an arm bursts through a blast door. This event causes a large and rapid increase in the surprise response signal, but no appreciable increase in the adrenaline response signal. At time 226, an event occurs in which a man screams that he is going to die. At time 228, the user is attacked by surprise and the user fumbles for a gun, causing a very large increase in the surprise related response signal 204. The foregoing events are exemplary of the type of events and mental reactions or responses that are determinable using the methods described herein.

Figure 11:
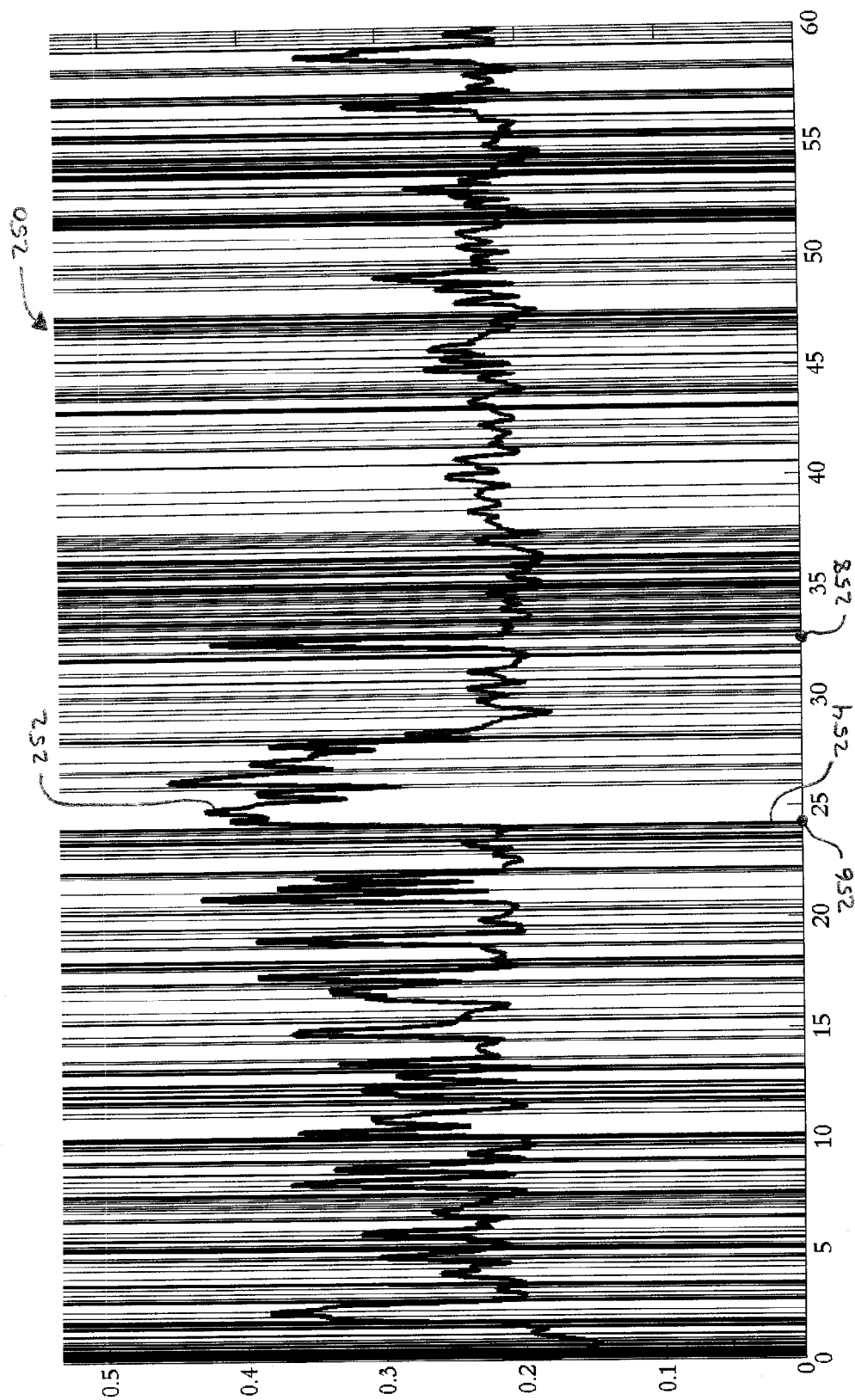
FIG. 11 is another graph of mental reaction signals from media analysis device shown in FIG. 1.

In another example, a graph 250 (FIG. 11) shows empirical results of using a sensor of mental engagement, based on Theta band EEG energy, and a sensor of attention during events in a period of time in which the user is playing another game. The mental engagement sensor produces response signal 252 while the attention sensor produces response signal 254. The response signal 254 of the attention sensor shows vertical lines in graph 250 where the user blinks. Amplitude of response signal 252 indicate levels of Theta band EEG energy in the user at different times while the user is playing the game. Increases in response signal 252 indicate an increase in Theta band EEG energy which corresponds to increased mental engagement of the user in the game. Decreases in the blink rate indicated by response signal 254 correspond to increases in attention of the user.

At a time 256, which is around 24 minutes, the user faces a very intense situation which leads to a rise in mental engagement and increase in attention. The rise in mental engagement is seen in engagement response signal 252 at time 256 as increased amplitude. The increase in the user's attention is seen in blink response signal 254 as a decrease in blink rate. Later in graph 250 at time 258, which is around 33 minutes, the user loses attention when a disengaging cut-scene and slow point in the game resumes. The loss of attention appears in graph 250 as a dramatic increase in the blink rate. Using information from the response signals 252 and 254, a game developer can decide if a game is having the response that is desired.

Figure 12:
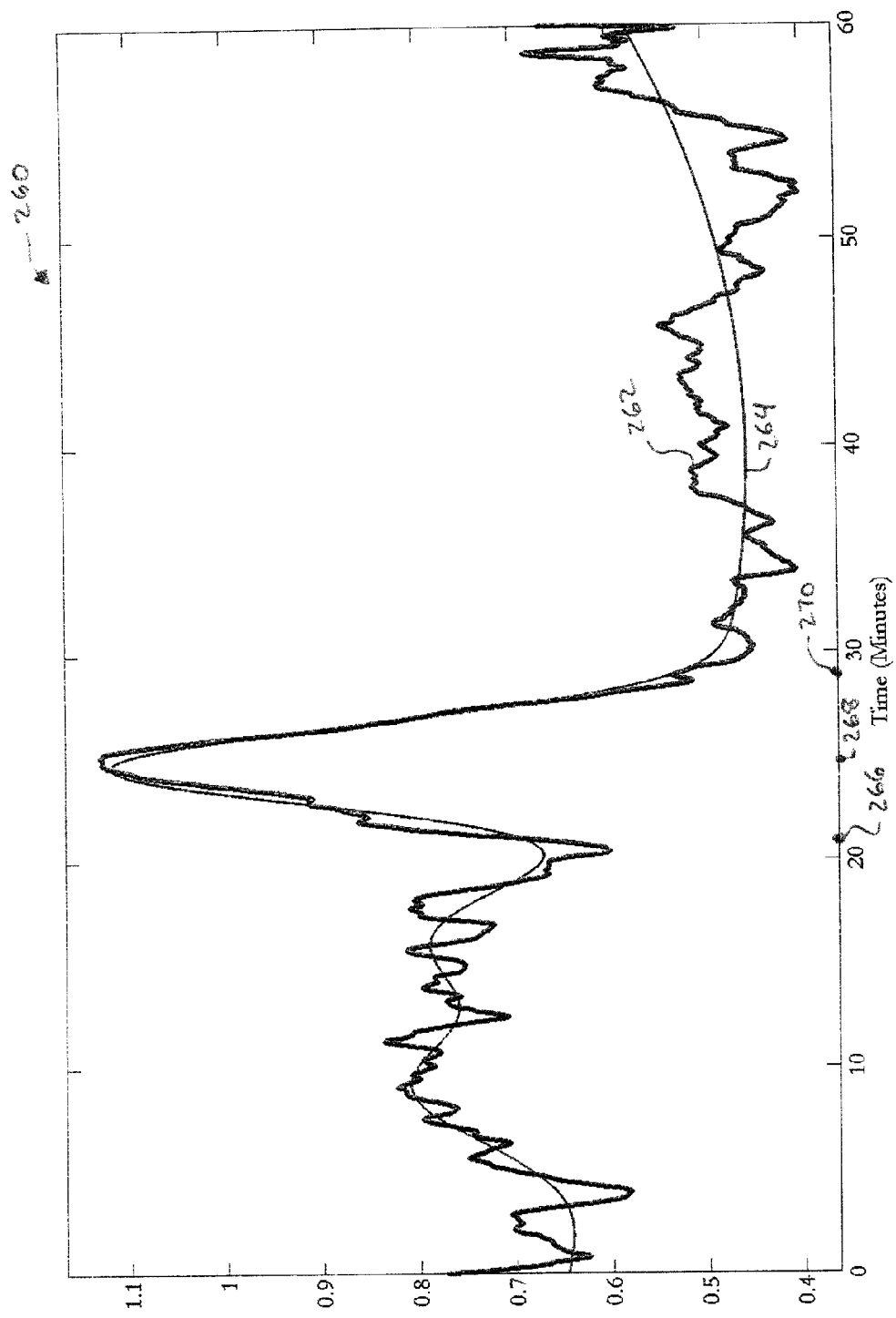
FIG. 12 is another graph of a mental reaction signal from media analysis device shown in FIG. 1.
Figure 13:
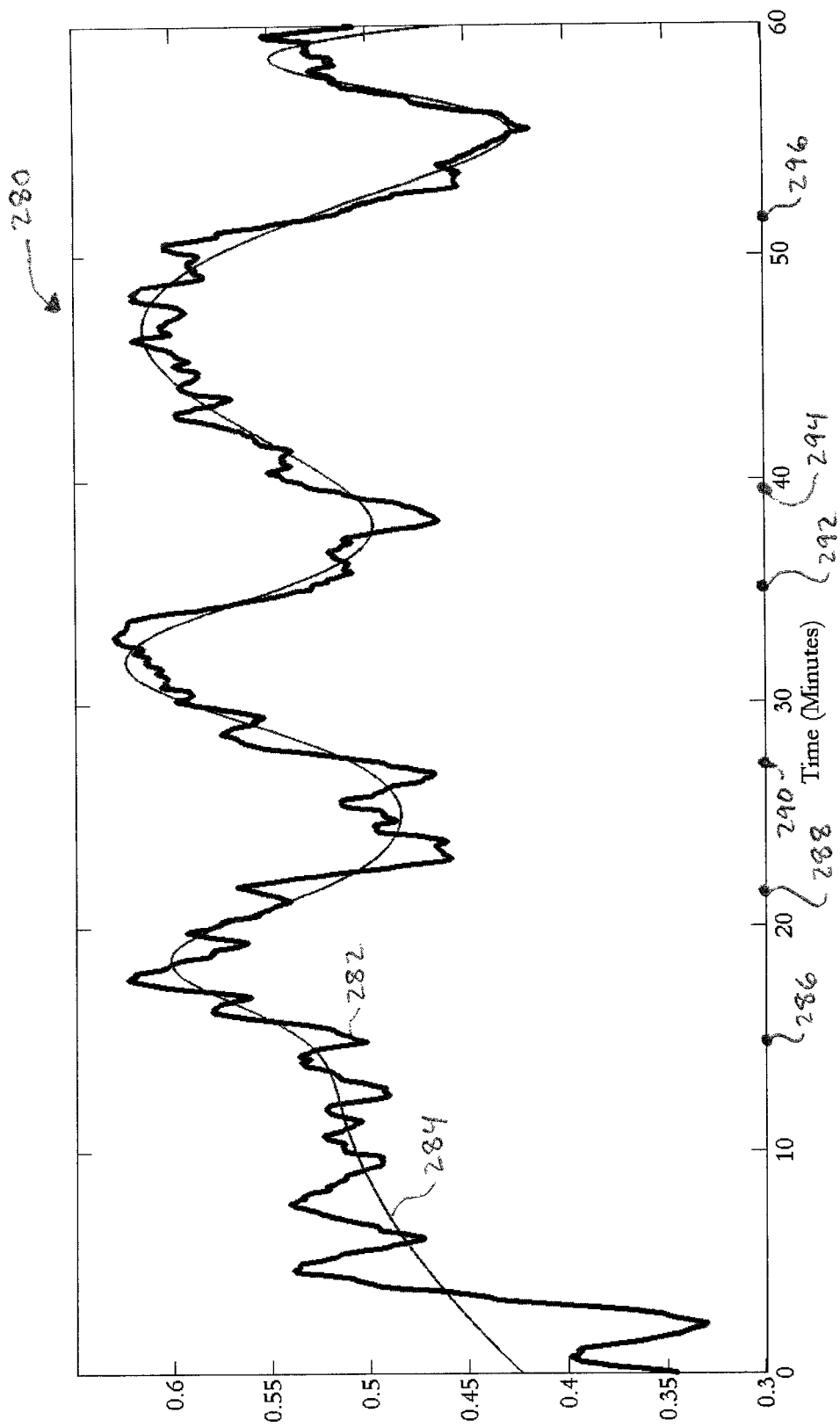
FIG. 13 is another graph of a mental reaction signal from media analysis device shown in FIG. 1.

Another example of empirical results gained by using mental responses in game development is shown in FIGS. 12 and 13, to illustrate a concept of balance. A game cannot constantly stimulate the user and keep the user attached, or interested; at some point the user attenuates to the stimulus of the game. In order to achieve a shock when the user is attenuated, greater and greater inputs have to be applied. A graph 260 (FIG. 12) shows a response signal 262 of mental engagement and a fit curve 264 of the response signal while the user is playing a certain game. While playing the game, the user's mental focus level modulates in relation to how engaged the user is in the game. Up to about time 266, the game media is interesting and the user remains engaged as noted by the relatively high levels of response signal 262 prior to time 266. At around time 266, the user faces a media event which includes a boss character that causes the user to become very engaged and excited as indicated by the peak in response signal 262 at time 268. However, the event becomes overengaged and mentally climaxes early, causing the response signal 262 to drop rapidly to a relatively lower level at time 270. After the drop in response signal 262, the user does not re-engage with the game and the user's mental engagement level, as indicated by response signal 262 drops below the original level seen at the beginning of the game experience.

Graph 260 illustrates the response signal of a user to an unbalanced game. An unbalanced game does not place evenly spaced challenges and fails to continually engage the user. At some point in an unbalanced game, a user will become sufficiently disengaged and stop playing the game. When the user stops playing the game because the game is not sufficiently engaging, the game developers have failed.

Graph 280 (FIG. 13) includes a response signal 282 and a fit curve 284 of a user's mental engagement response to a balanced game. In the balanced game, the mental engagement level, response signal 282, modulates up and down in a periodic fashion. This periodic fashion depicts the episodic nature of the balanced game, which presents sets of problems for the user to challenge, which causes the user to continually become reengaged in the game. The balanced game stimulates the player at times 286, 290 and 294, while letting the user relax at times 288, 292 and 296. In this way the user is allowed to relax between challenges. A well balanced game, like a well written book, should slowly pull the user in and keep the user engaged while slowly building up to the climax of the story.

While a number of exemplary aspects and embodiments have been discussed above, those of skill in the art will recognize certain modifications, permutations, additions and sub-combinations thereof. For example, the above methods and techniques can be applied to the production of movies, television programs or other audio/visual and other media where a developer is interested in the response of the user to the media. It is therefore intended that the following appended claims and claims hereafter introduced are interpreted to include all such modifications, permutations, additions and sub-combinations as are within their true spirit and scope.

What is claimed is:

1. A method comprising:
    applying, using a processor, a first adjustment factor to first data gathered from a subject exposed to a stimulus to form first adjusted data;
    applying, using the processor, a second adjustment factor to the first data to form second adjusted data;
    applying, using the processor, a third adjustment factor to second data gathered from the subject to form third adjusted data;
    applying, using the processor, a fourth adjustment factor to the second data to form fourth adjusted data;
    calculating, using the processor, a sum based on the first adjusted data, the second adjusted data, the third adjusted data, and the fourth adjusted data;
    determining, using the processor, a mental state of the subject based on the sum; and
    adjusting, using the processor, at least one of the first adjustment factor, the second adjustment factor, the third adjustment factor, or the fourth adjustment factor based on a characteristic of at least one of the first data or the second data.

2. The method of claim 1, wherein the first adjustment factor is based on a first proportion of the first data used relative to the second data.

3. The method of claim 1, wherein the fourth adjustment factor is based on a second proportion of the second data used relative to the first data.

4. The method of claim 1, wherein the second adjustment factor is based on a first confidence in the first data.

5. The method of claim 4, wherein the first confidence is based on a first diagnosis of data quality of a first sensor used to gather the first data.

6. The method of claim 1, wherein the third adjustment factor is based on a second confidence in the second data.

7. The method of claim 6, wherein the second confidence is based on a second diagnosis of data quality of a second sensor used to gather the second data.

8. The method of claim 1, wherein the second adjustment factor is based on a first derivative of the first data and a first offset.

9. The method of claim 1, wherein the fourth adjustment factor is based on a second derivative of the second data and a second offset.

10. The method of claim 1 further including applying a fifth adjustment factor to the sum to form fifth adjusted data.

11. The method of claim 10 wherein one of the first adjustment factor or the second adjustment factor is based on a first confidence in the first data and one of the third adjustment factor or the fourth adjustment factor is based on a second confidence in the second data, and the fifth adjustment factor is based on a coherence of the first confidence and the second confidence.

12. The method of claim 10 wherein determining the mental state of the subject is based on the fifth adjusted data.

13. The method of claim 1, wherein the first data is gathered from a first modality and the second data is gathered from a second modality.

14. The method of claim 13, wherein the first data is electroencephalographic data and the second data is heart rate data.

15. The method of claim 13, wherein the first data is electroencephalographic data and the second data is blood oxygen level data.

16. The method of claim 15, wherein the blood oxygen level data is based on a breathing pattern.

17. The method of claim 13, wherein the first data is electroencephalographic data and the second data is head movement data.

18. The method of claim 17, wherein the head movement data includes movement in three directions.

19. The method of claim 18 further including applying a fifth adjustment factor to the head movement data, the fifth adjustment factor determined by:
calculating a first square of movement data in an x direction;
calculating a second square of movement data in a y direction;
calculating a third square of movement data in a z direction;
summing the first, second and third squares; and
calculating a square root of the sum of the first, second and third squares.

20. The method of claim 1 further including changing one or more of the first adjustment factor, the second adjustment factor, the third adjustment factor, or the fourth adjustment factor based on a rate of change of at least one of the first data or the second data.

21. The method of claim 1 further including changing one or more of the first adjustment factor, the second adjustment factor, the third adjustment factor, or the fourth adjustment factor during gathering of at least one of the first data or the second data.

22. The method of claim 1 further including changing one or more of the first adjustment factor, the second adjustment factor, the third adjustment factor, or the fourth adjustment factor based on at least one of the first data or the second data exceeding a threshold.

23. The method of claim 22, wherein the threshold is based on a physiological response.

24. A system comprising:
a memory including machine readable instructions; and
a processor to execute the instructions to analyze first data and second data gathered from a subject exposed to a stimulus by:
applying a first adjustment factor to the first data to form first adjusted data;
applying a second adjustment factor to the first data to form second adjusted data;
applying a third adjustment factor to second data gathered from the subject to form third adjusted data;
applying a fourth adjustment factor to the second data to form fourth adjusted data; and
calculating a sum based on the first adjusted data, the second adjusted data, the third adjusted data, and the fourth adjusted data;
the instructions to cause the processor to determine a mental state of the subject based on the sum, and to adjust at least one of the first adjustment factor, the second adjustment factor, the third adjustment factor, or the fourth adjustment factor based on a characteristic of at least one of the first data or the second data.

25. The system of claim 24, wherein the first adjustment factor is based on a first proportion of the first data used relative to the second data.

26. The system of claim 24, wherein the fourth adjustment factor is based on a second proportion of the second data used relative to the first data.

27. The system of claim 24, wherein the second adjustment factor is based on a first confidence in the first data.

28. The system of claim 24, wherein the first confidence is based on a first diagnosis of data quality of a first sensor used to gather the first data.

29. The system of claim 24, wherein the third adjustment factor is based on a second confidence in the second data.

30. The system of claim 29, wherein the second confidence is based on a second diagnosis of data quality of a second sensor used to gather the second data.

31. The system of claim 24, wherein the second adjustment factor is based on a first derivative of the first data and a first offset.

32. The system of claim 24, wherein the fourth adjustment factor is based on a second derivative of the second data and a second offset.

33. The system of claim 24, wherein the processor is to apply a fifth adjustment factor to the sum to form fifth adjusted data.

34. The system of claim 33, wherein one of the first adjustment factor or the second adjustment factor is based on a first confidence in the first data and one of the third adjustment factor or the fourth adjustment factor is based on a second confidence in the second data, and the fifth adjustment factor is based on a coherence of the first confidence and the second confidence.

35. The system of claim 33, wherein the processor is to determine the mental state of the subject based on the fifth adjusted data.

36. The system of claim 24, wherein the first data is gathered from a first modality and the second data is gathered from a second modality.

37. The system of claim 36, wherein the first data is electroencephalographic data and the second data is heart rate data.

38. The system of claim 36, wherein the first data is electroencephalographic data and the second data is blood oxygen level data.

39. The system of claim 38, wherein the blood oxygen level data is based on a breathing pattern.

40. The system of claim 36, wherein the first data is electroencephalographic data and the second data is head movement data.

41. The system of claim 40, wherein the head movement data includes movement in three directions.

42. The system of claim 41, wherein the processor is to apply a fifth adjustment factor to the head movement data, the processor to determine the fifth adjustment factor by:
calculating a first square of movement data in an x direction;
calculating a second square of movement data in a y direction;
calculating a third square of movement data in a z direction;
summing the first, second and third squares; and
calculating a square root of the sum of the first, second and third squares.

43. The system of claim 24, wherein the processor is to change one or more of the first adjustment factor, the second adjustment factor, the third adjustment factor, or the fourth adjustment factor based on a rate of change of at least one of the first data or the second data.

44. The system of claim 24, wherein the processor is to change one or more of the first adjustment factor, the second adjustment factor, the third adjustment factor, or the fourth adjustment factor during gathering of at least one of the first data or the second data.

45. The system of claim 24, wherein the processor is to change one or more of the first adjustment factor, the second adjustment factor, the third adjustment factor, or the fourth adjustment factor based on at least one of the first data or the second data exceeding a threshold.

46. The system of claim 45, wherein the threshold is based on a physiological response.

47. A tangible machine readable storage medium comprising instructions which, when executed, cause a machine to at least:
   apply a first adjustment factor to first data gathered from a subject exposed to a stimulus to form first adjusted data;
   apply a second adjustment factor to the first data to form second adjusted data;
   apply a third adjustment factor to second data gathered from the subject to form third adjusted data;
   apply a fourth adjustment factor to the second data to form fourth adjusted data;
   calculate a sum based on the first adjusted data, the second adjusted data, the third adjusted data, and the fourth adjusted data;
   determine a mental state of the subject based on the sum; and
   adjust at least one of the first adjustment factor, the second adjustment factor, the third adjustment factor, or the fourth adjustment factor based on a characteristic of at least one of the first data or the second data.

48. The medium of claim 47, wherein the first adjustment factor is based on a first proportion of the first data used relative to the second data and the fourth adjustment factor is based on a second proportion of the second data used relative to the first data.

49. The medium of claim 47, wherein the second adjustment factor is based on a first confidence in the first data and the third-fifth adjustment factor is based on a second confidence in the second data.

50. The medium of claim 49, wherein the first confidence is based on a first diagnosis of data quality of a first sensor used to gather the first data and the second confidence is based on a second diagnosis of data quality of a second sensor used to gather the second data.

51. The medium of claim 47, wherein the second adjustment factor is based on a first derivative of the first data and a first offset and the fourth adjustment factor is based on a second derivative of the second data and a second offset.

52. The medium of claim 47, wherein the instructions further cause the machine to apply a fifth adjustment factor to the sum to form fifth adjusted data.

53. The medium of claim 52, wherein one of the first adjustment factor or the second adjustment factor is based on a first confidence in the first data, one of the third adjustment factor or the fourth adjustment factor is based on a second confidence in the second data, and the fifth adjustment factor is based on a coherence of the first confidence and the second confidence.

54. The medium of claim 52, wherein the instructions cause the machine to determine the mental state of the subject based on the fifth adjusted data.

55. The medium of claim 47, wherein the first data is gathered from a first modality and the second data is gathered from a second modality.

56. The medium of claim 55, wherein the first data is electroencephalographic data and the second data is heart rate data.

57. The medium of claim 55, wherein the first data is electroencephalographic data and the second data is blood oxygen level data.

58. The medium of claim 57, wherein the blood oxygen level data is based on a breathing pattern.

59. The medium of claim 55, wherein the first data is electroencephalographic data and the second data is head movement data.

60. The medium of claim 59, wherein the head movement data includes movement in three directions.

61. The medium of claim 60, wherein the instructions further cause the machine to apply a fifth adjustment factor to the head movement data, the fifth adjustment factor determined by:
   calculating a first square of movement data in an x direction;
   calculating a second square of movement data in a y direction;
   calculating a third square of movement data in a z direction;
   summing the first, second and third squares; and
   calculating a square root of the sum of the first, second and third squares.

62. The medium of claim 47, wherein the instructions further cause the machine to change one or more of the first adjustment factor, the second adjustment factor, the third adjustment factor, or the fourth adjustment factor based on a rate of change of at least one of the first data or the second data.

63. The medium of claim 47, wherein the instructions further cause the machine to change one or more of the first adjustment factor, the second adjustment factor, the third adjustment factor, or the fourth adjustment factor during gathering of at least one of the first data or the second data.

64. The medium of claim 47, wherein the instructions further cause the machine to change one or more of the first adjustment factor, the second adjustment factor, the third adjustment factor, or the fourth adjustment factor based on at least one of the first data or the second data exceeding a threshold, the threshold based on a physiological response.

* * * * *